(12) United States Patent
Nakayama et al.

(10) Patent No.: US 9,416,148 B2
(45) Date of Patent: Aug. 16, 2016

(54) PHOSPHORUS COMPOUND AND TRANSITION METAL COMPLEX OF THE SAME

(71) Applicant: TAKASAGO INTERNATIONAL CORPORATION, Tokyo (JP)

(72) Inventors: Yuji Nakayama, Kanagawa (JP); Naota Yokoyama, Tokyo (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 14/638,761

(22) Filed: Mar. 4, 2015

(65) Prior Publication Data

US 2015/0307531 A1  Oct. 29, 2015

(30) Foreign Application Priority Data

Apr. 25, 2014  (JP) .................................. 2014-091768

(51) Int. Cl.
| | | |
|---|---|---|
| *C07F 9/572* | (2006.01) | |
| *C07F 9/50* | (2006.01) | |
| *C07F 15/00* | (2006.01) | |

(52) U.S. Cl.
CPC ............. *C07F 9/5031* (2013.01); *C07F 9/5722* (2013.01); *C07F 9/5728* (2013.01); *C07F 15/006* (2013.01)

(58) Field of Classification Search
CPC ............................ C07F 9/5722; C07F 9/5728
See application file for complete search history.

(56) References Cited

PUBLICATIONS

Sheung Chun To et al., Highly efficient carbazolyl-derived phosphine ligands: application to sterically hindered biaryl couplings, Chemical Communications, Mar. 29, 2011, vol. 47, pp. 5079-5081.

*Primary Examiner* — Shawquia Jackson
(74) *Attorney, Agent, or Firm* — Sughrue Mion, PLLC

(57) ABSTRACT

The present invention provides a compound represented by general formula (1) and a transition metal complex containing the compound as a ligand:

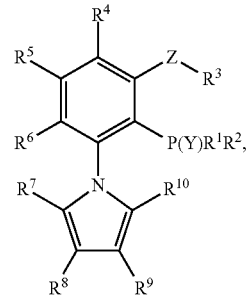

(1)

wherein $R^1$ to $R^{10}$, N, P, Y, and Z have the meanings as defined in DESCRIPTION.

6 Claims, No Drawings

PHOSPHORUS COMPOUND AND TRANSITION METAL COMPLEX OF THE SAME

TECHNICAL FIELD

The present invention relates to a novel phosphorus compound and a transition metal complex comprising the phosphorus compound as a ligand.

BACKGROUND ART

Recently, various transition metal complexes constituted of transition metal species and ligands have been used as catalysts for organic synthesis reactions. As a factor for the expression of the performance or activity of such a catalyst, it is well known that not only the transition metal species but also the ligand plays an important role in a metal complex. For this reason, numerous compounds having coordinating nature, including phosphorus compounds, have been developed as ligands so far. Moreover, for organic synthesis reactions catalyzed by metal complexes, optimum catalysts for a wide variety of reactants can be prepared by appropriately combining a transition metal species and a ligand. Hence, the research and development of such organic synthesis reactions catalyzed by metal complexes are still being actively carried out. For putting a catalytic organic synthesis reaction into an industrial use, the variety of ligands greatly contributes to the optimization and efficiency improvement of the reaction, because the number of transition metals is limited. Actually, however, even with the use of ligands developed so far, the catalytic activity and the reaction selectivity are insufficient in some reactions. Even if the performance of a ligand is extremely efficient, it is difficult to apply the ligand to an industrial catalytic organic synthesis reaction, unless the ligand can be mass produced easily at low costs. From the above-described viewpoints, the development of a novel phosphorus compound which can be mass produced easily at low costs and which can be used as an efficient ligand is still eagerly awaited under the current situation.

An example of the phosphorus compounds is the N-(2-phosphinophenyl)carbazole represented by the following general formula (2), where R represents an alkyl group or an aryl group, developed by Fuk Yee Kwong et al. (Sheung Chun and Fuk Yee Kwong, "Highly efficient carbazolyl-derived phosphine ligands: applications to sterically hindered biaryl couplings", Chemical Communications, 2011, 47, 5079). Reportedly, this phosphorus compound works as an extremely efficient ligand in a cross-coupling reaction between an aryl halide and an arylboronic acid catalyzed by palladium, which is one of the transition metals (that is, the Suzuki-Miyaura coupling reaction). However, the synthesis of the phosphorus compound inevitably involves the Ullmann reaction which requires high temperature and long time, and which is poor in reaction selectivity and isolated yield, and the halogen-lithium exchange and the phosphination reaction which require extremely low-temperature. For this reason, it is extremely difficult to mass produce this phosphorus compound at low costs.

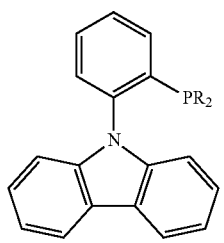

(2)

SUMMARY OF INVENTION

The present invention has been made in view of the above-described problems. Specifically, an object of the present invention is to provide a phosphorus compound and a transition metal complex thereof which can be mass produced easily at low costs, and further which can be used as a ligand useful for catalytic organic synthesis reactions or as a catalyst useful for organic synthesis reactions.

The present inventors have conducted intensive study to achieve the above-described object, and consequently found that a novel phosphorus compound represented by the following general formula (1) not only can be synthesized easily at low costs, but also can serve as a ligand having excellent performance. Moreover, the present inventors have found that a transition metal complex containing the phosphorus compound as a ligand can serve as a catalyst excellent for organic synthesis reactions, for example, as a catalyst extremely useful for a cross-coupling reaction or the like. These findings have led to the completion of the present invention.

Specifically, the present invention includes the following [1] to [6].

[1] A phosphorus compound represented by general formula (1):

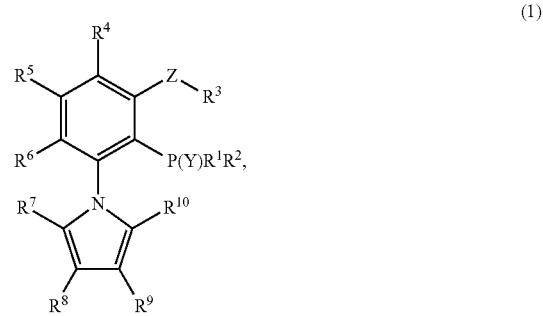

(1)

wherein $R^1$ and $R^2$ each independently represent a hydrogen atom, an alkyl group, an alkenyl group which may have a substituent(s), an aryl group which may have a substituent(s), a heteroaryl group which may have a substituent(s), an aralkyl group which may have a substituent(s), an alkoxy group which may have a substituent(s), or a halogeno group; $R^3$ represents an alkyl group, an aryl group which may have a substituent(s), or an aralkyl group which may have a substituent(s); $R^4$, $R^5$, $R^6$, $R^7$, $R^8$, $R^9$, and $R^{10}$ each independently represent a hydrogen atom, an alkyl group, an alkenyl group which may have a substituent(s), an aryl group which may have a substituent(s), or an aralkyl group which may have a substituent (s); N represents a nitrogen atom; P represents a phosphorus atom; Y represents lone pair electrons, an oxo group, or a thioxo group; Z represents an oxy group or a thioxy group; $R^1$ and $R^2$ may be bonded to each other to form a ring which contains P and may have a substituent (s); and each of the pairs of $R^4$ and $R^5$, $R^5$ and $R^6$, $R^7$ and $R^8$, $R^8$ and $R^9$, and $R^9$ and $R^{10}$ may be bonded to each other to form an unsaturated hydrocarbon ring which is fused with the benzene ring or the pyrrole ring and may have a substituent(s).

[2] The phosphorus compound according to the above-described [1], wherein $R^1$ and $R^2$ each independently represent an alkyl group, an alkenyl group which may have a substituent (s), an aryl group which may have a substituent(s), a heteroaryl group which may have a substituent(s), or an aralkyl group which may have a substituent(s), and Y is lone pair electrons.

[3] The phosphorus compound according to the above-described [1] or [2], wherein
Z is an oxy group.
[4] A transition metal complex comprising:
a transition metal; and
the phosphorus compound according to any one of the above-described [1] to [3] as a ligand.
[5] The transition metal complex according to the above-described [4], wherein
the transition metal is selected from the group consisting of iron, cobalt, nickel, copper, ruthenium, rhodium, palladium, silver, osmium, iridium, platinum, and gold.
[6] The transition metal complex according to the above-described [5], wherein
the transition metal is palladium.

Specifically owing to an effect of the $R^3Z$ group ($R^3$ represents an alkyl group, an aryl group which may have a substituent(s), or an aralkyl group which may have a substituent(s), and Z represents an oxy group or a thioxy group), the above-described novel phosphorus compound represented by general formula (1) (hereinafter, referred to as phosphorus compound (1) of the present invention) can be produced more easily at lower costs than the above-described known phosphorus compound represented by general formula (2) (hereinafter, referred to as conventional compound (2)), and it is possible to avoid the Ullmann reaction and the extremely low-temperature reaction, which have caused the problem so far. It has been found that the $R^3Z$ group contributes to not only improvement in production efficiently of the phosphorus compound of the present invention, but also the improvement in the performance of the phosphorus compound used as a ligand. For example, when one of phosphorus compounds (1) of the present invention having such a structure that the portions other than the $R^3Z$ group are the same as those of conventional compound (2) was used as a ligand for a Suzuki-Miyaura coupling reaction, it was found that the catalytic activity was improved by 1.9 times or more in comparison with conventional compound (2). Moreover, in a cross-coupling reaction between an aryl halide and an amine catalyzed by palladium (that is, the Buchwald-Hartwig amination reaction), it was revealed that the amount of impurities by-produced was reduced to 1/10 or less of the amount of impurities by-produced when conventional compound (2) was used.

In sum, phosphorus compound (1) of the present invention is useful as a ligand for catalytic organic synthesis reactions using a transition metal species, and also can be produced easily. Meanwhile, a transition metal complex (hereinafter, referred to as complex (3) of the present invention) containing phosphorus compound (1) of the present invention as a ligand is useful as a catalyst for organic synthesis reactions. For example, a complex of palladium, which is one of the transition metals, and phosphorus compound (1) of the present invention is extremely useful as a catalyst for cross-coupling reactions and the like, and these reactions make it possible to efficiently produce aromatic compounds and the like.

DESCRIPTION OF EMBODIMENTS

Hereinafter, phosphorus compound (1) of the present invention will be described in further detail.

In general formula (1), $R^1$ and $R^2$ each independently represent a hydrogen atom, an alkyl group, an alkenyl group which may have a substituent(s), an aryl group which may have a substituent(s), a heteroaryl group which may have a substituent(s), an aralkyl group which may have a substituent(s), an alkoxy group which may have a substituent(s), or a halogeno group, preferably represent an alkyl group, an alkenyl group which may have a substituent(s), an aryl group which may have a substituent(s), a heteroaryl group which may have a substituent(s), or an aralkyl group which may have a substituent(s), and more preferably represent an alkyl group or an aryl group which may have a substituent(s).

The alkyl group is, for example, an alkyl group having 1 to 30 carbon atoms, preferably an alkyl group having 1 to 20 carbon atoms, and more preferably an alkyl group having 1 to 10 carbon atoms, which may be linear, branched, or cyclic. Specifically, the alkyl group may be a methyl (Me) group, an ethyl group, a n-propyl group, a 2-propyl ($^i$Pr) group, a cyclopropyl group, a n-butyl group, a 2-butyl group, an isobutyl group, a tert-butyl ($^t$Bu) group, a cyclobutyl group, a n-pentyl group, a 2-pentyl group, a 3-pentyl group, a tert-pentyl group, a 2-methylbutyl group, a 3-methylbutyl group, a 2-methylbutan-3-yl group, a 2,2-dimethylpropyl group, a cyclopentyl group, a n-hexyl group, a 2-hexyl group, a 3-hexyl group, a tert-hexyl group, a 2-methylpentyl group, a 3-methylpentyl group, a 4-methylpentyl group, a 2-methylpentan-3-yl group, a 2-methylpentan-4-yl group, a 3-methylpentan-2-yl group, a 3-methylpentan-3-yl group, a 2,2-dimethylbutyl group, a 3,3-dimethylbutyl group, a 2,2-dimethylbutan-3-yl group, a cyclohexyl (Cy) group, a 1-adamantyl (1-Ad) group, a 2-adamantyl (2-Ad) group, or the like. Preferred specific examples thereof include a 2-propyl group, a cyclohexyl group, and the like.

The alkenyl group is, for example, an alkenyl group having 2 to 20 carbon atoms, preferably an alkenyl group having 2 to 14 carbon atoms, and more preferably an alkenyl group having 2 to 8 carbon atoms, which may be linear, branched, or cyclic. Specifically, the alkenyl group may be a vinyl group, a 1-propenyl group, a 2-propenyl group, an allyl group, a 1-cyclohexenyl group, a 1-styryl group, a 2-styryl group, or the like.

The aryl group is, for example, an aryl group having 6 to 18 carbon atoms, preferably an aryl group having 6 to 14 carbon atoms, and more preferably an aryl group having 6 to 12 carbon atoms. Specifically, the aryl group may be a phenyl (Ph) group, a 1-naphthyl group, a 2-naphthyl group, a 2-biphenyl group, a 4-biphenyl group, or the like. A preferred specific example is a phenyl group.

The heteroaryl group is, for example, a heteroaryl group having 1 to 12 carbon atoms, preferably a heteroaryl group having 2 to 10 carbon atoms, and more preferably a heteroaryl group having 4 to 8 carbon atoms. Specifically, the heteroaryl group may be a 2-furyl group, a 3-furyl group, a 2-thienyl group, a 3-thienyl group, a 2-benzofuryl group, a 3-benzofuryl group, a 2-benzothienyl group, a 3-benzothienyl group, or the like.

The aralkyl group is, for example, an aralkyl group having 7 to 24 carbon atoms, preferably an aralkyl group having 7 to 16 carbon atoms, and more preferably an aralkyl group having 7 to 13 carbon atoms, which may be linear, branched, or cyclic. Specifically, the aralkyl group may be a benzyl (Bn) group, a 1-phenylethyl group, a 2-phenylethyl group, a 1-phenylpropyl group, a 2-phenylpropyl group, a 3-phenylpropyl group, a 1-phenyl-2-propyl group, a 2-phenyl-2-propyl group, a 1-phenylcyclopropyl group, a 2-phenylcyclopropyl group, a 1-indanyl group, a 2-indanyl group, a 1,1-dimethyl-2-phenylethyl group, a 9-fluorenyl group, or the like.

The alkoxy group is, for example, an alkoxy group having 1 to 10 carbon atoms, and preferably an alkoxy group having 1 to 4 carbon atoms. Specifically, the alkoxy group may be a methoxy group, an ethoxy group, a 1-propoxy group, a 2-propoxy group, a 1-butoxy group, a 2-butoxy group, a tert-butoxy group, or the like.

The halogeno group may be a fluoro group, a chloro group, a bromo group, or an iodo group.

$R^1$ and $R^2$ may be bonded to each other to form a ring which contains the phosphorus atom and may have a substituent(s). Specific examples of such a ring include a phospholane ring, a phosphole ring, a phosphinane ring, a phosphinine ring, and the like.

Substituents which the alkenyl group, the aryl group, the heteroaryl group, the aralkyl group, and the alkoxy group represented by each of $R^1$ and $R^2$, and the phosphorus atom-containing ring formed by $R^1$ and $R^2$ bonded to each other may have include alkyl groups, halogenoalkyl groups, aryl groups, heteroaryl groups, aralkyl groups, alkoxy groups, halogeno groups, and the like. Of these substituents, the alkyl groups, the aryl groups, the heteroaryl groups, the aralkyl groups, the alkoxy groups, and the halogeno groups are the same as those listed in the detailed description of $R^1$ and $R^2$. The halogenoalkyl groups include groups which are the same as the above-described alkyl groups, except that at least one hydrogen atom therein is replaced by a halogen atom, and specifically include trifluoromethyl groups and the like.

In general formula (1), $R^3$ represents an alkyl group, an aryl group which may have a substituent (s), or an aralkyl group which may have a substituent(s), and preferably represents an alkyl group.

The alkyl group is, for example, an alkyl group having 1 to 30 carbon atoms, preferably an alkyl group having 1 to 20 carbon atoms, and more preferably an alkyl group having 1 to 10 carbon atoms, which may be linear, branched, or cyclic. Specifically, the alkyl group may be a methyl group, an ethyl group, a n-propyl group, a 2-propyl group, a cyclopropyl group, a n-butyl group, a 2-butyl group, an isobutyl group, a tert-butyl group, a cyclobutyl group, a n-pentyl group, a 2-pentyl group, a 3-pentyl group, a tert-pentyl group, a 2-methylbutyl group, a 3-methylbutyl group, a 2-methylbutan-3-yl group, a 2,2-dimethylpropyl group, a cyclopentyl group, a n-hexyl group, a 2-hexyl group, a 3-hexyl group, a tert-hexyl group, a 2-methylpentyl group, a 3-methylpentyl group, a 4-methylpentyl group, a 2-methylpentan-3-yl group, a 2-methylpentan-4-yl group, a 3-methylpentan-2-yl group, a 3-methylpentan-3-yl group, a 2,2-dimethylbutyl group, a 3,3-dimethylbutyl group, a 2,2-dimethylbutan-3-yl group, a cyclohexyl group, a 1-adamantyl group, a 2-adamantyl group, or the like. Preferred specific examples thereof include a methyl group, a 2-propyl group, a tert-butyl group, and the like.

The aryl group is, for example, an aryl group having 6 to 18 carbon atoms, preferably an aryl group having 6 to 14 carbon atoms, and more preferably an aryl group having 6 to 10 carbon atoms. Specifically, the aryl group may be a phenyl group, a 1-naphthyl group, a 2-naphthyl group, or the like.

The aralkyl group is, for example, an aralkyl group having 7 to 24 carbon atoms, preferably an aralkyl group having 7 to 16 carbon atoms, and more preferably an aralkyl group having 7 to 10 carbon atoms, which may be linear or branched. Specifically, the aralkyl group may be a benzyl group, a 1-phenylethyl group, a 2-phenylethyl group, a 1-phenylpropyl group, a 2-phenylpropyl group, a 3-phenylpropyl group, a 1-phenyl-2-propyl group, a 2-phenyl-2-propyl group, a 1,1-dimethyl-2-phenylethyl group, or the like.

Substituents which the aryl group or the aralkyl group represented by $R^3$ may have include alkyl groups, aryl groups, and aralkyl groups. These substituents are the same as those listed in the detailed description of $R^3$.

In general formula (1), $R^4$ to $R^{10}$ each independently represent a hydrogen atom, an alkyl group, an alkenyl group which may have a substituent(s), an aryl group which may have a substituent(s), or an aralkyl group which may have a substituent(s), and preferably represent a hydrogen atom, an alkyl group, or an alkenyl group which may have a substituent (s) It is more preferable that $R^4$ to $R^6$ each represent a hydrogen atom, and $R^7$ to $R^{10}$ each independently represent a hydrogen atom, an alkyl group, or an alkenyl group which may have a substituent(s).

The alkyl group is, for example, an alkyl group having 1 to 30 carbon atoms, preferably an alkyl group having 1 to 20 carbon atoms, and more preferably an alkyl group having 1 to 6 carbon atoms, which may be linear, branched, or cyclic. Specifically, the alkyl group may be a methyl group, an ethyl group, a n-propyl group, a 2-propyl group, a cyclopropyl group, a n-butyl group, a 2-butyl group, an isobutyl group, a tert-butyl group, a cyclobutyl group, a n-pentyl group, a 2-pentyl group, a 3-pentyl group, a tert-pentyl group, a 2-methylbutyl group, a 3-methylbutyl group, a 2-methylbutan-3-yl group, a 2,2-dimethylpropyl group, a cyclopentyl group, a n-hexyl group, a 2-hexyl group, a 3-hexyl group, a tert-hexyl group, a 2-methylpentyl group, a 3-methylpentyl group, a 4-methylpentyl group, a 2-methylpentan-3-yl group, a 2-methylpentan-4-yl group, a 3-methylpentan-2-yl group, a 3-methylpentan-3-yl group, a 2,2-dimethylbutyl group, a 3,3-dimethylbutyl group, a 2,2-dimethylbutan-3-yl group, a cyclohexyl group, or the like. Preferred specific examples thereof include a methyl group, an ethyl group, a n-propyl group, and the like.

The alkenyl group is, for example, an alkenyl group having 2 to 20 carbon atoms, preferably an alkenyl group having 2 to 14 carbon atoms, and more preferably an alkenyl group having 2 to 8 carbon atoms, which may be linear, branched, or cyclic. Specifically, the alkenyl group may be a vinyl group, a 1-propenyl group, a 2-propenyl group, an allyl group, a 1-cyclohexenyl group, a 1-styryl group, a 2-styryl group, or the like. Preferred specific examples thereof include a vinyl group and the like.

The aryl group is, for example, an aryl group having 6 to 18 carbon atoms, preferably an aryl group having 6 to 14 carbon atoms, and more preferably an aryl group having 6 to 10 carbon atoms. Specifically, the aryl group may be a phenyl group, a 1-naphthyl group, a 2-naphthyl group, or the like.

The aralkyl group is, for example, an aralkyl group having 7 to 24 carbon atoms, preferably an aralkyl group having 7 to 16 carbon atoms, and more preferably an aralkyl group having 7 to 10 carbon atoms, which may be linear or branched. Specifically, the aralkyl group may be a benzyl group, a 1-phenylethyl group, a 2-phenylethyl group, a 1-phenylpropyl group, a 2-phenylpropyl group, a 3-phenylpropyl group, a 1-phenyl-2-propyl group, a 2-phenyl-2-propyl group, a 1,1-dimethyl-2-phenylethyl group, or the like.

Each of the pairs of $R^4$ and $R^5$, $R^5$ and $R^6$, $R^7$ and $R^8$, $R^8$ and $R^9$, and $R^9$ and $R^{10}$ may be bonded to each other to form an unsaturated hydrocarbon ring which is fused with the benzene ring or the pyrrole ring and may have a substituent(s). Specific examples of such a ring include a cyclopentene ring, a cyclohexene ring, a cycloheptene ring, a benzene ring, and the like, and preferred specific examples thereof include a cyclohexene ring and a benzene ring.

Substituents which the alkenyl group, the aryl group, or the aralkyl group represented by each of $R^4$, $R^5$, $R^6$, $R^7$, $R^8$, $R^9$, and $R^{10}$ and the unsaturated hydrocarbon ring fused with the benzene ring or the pyrrole ring formed by each of the pairs of $R^4$ and $R^5$, $R^5$ and $R^6$, $R^7$ and $R^8$, $R^8$ and $R^9$, and $R^9$ and $R^{10}$ bonded to each other may have include alkyl groups, aryl groups, and aralkyl groups. These substituents are the same as those listed in the detailed description of $R^4$ to $R^{10}$.

In general formula (1), N represents a nitrogen atom, and P represents a phosphorus atom. Y represents lone pair electrons, an oxo group, or a thioxo group, and preferably represents lone pair electrons. Z represents an oxy group or a thioxy group, and preferably represents an oxy group.

Although the present invention is not limited to the following examples at all, preferred specific examples of phosphorus compound (1) of the present invention include compounds (1-1) to (1-28) shown below and the like, and particularly preferred specific examples thereof include compounds (1-1) to (1-7) and the like.

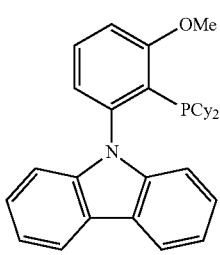
(1-1)

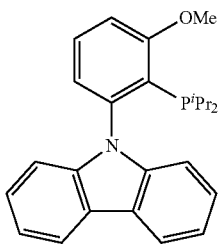
(1-2)

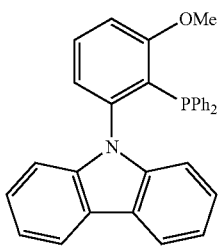
(1-3)

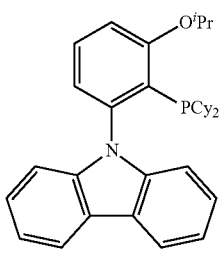
(1-4)

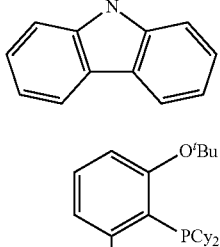
(1-5)

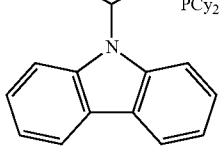

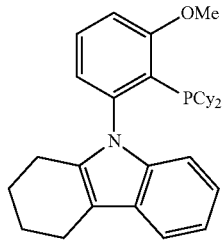
(1-6)

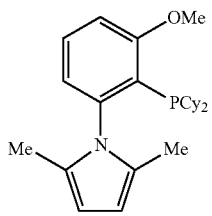
(1-7)

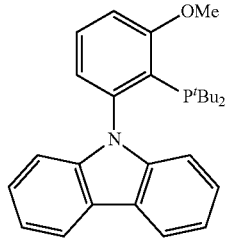
(1-8)

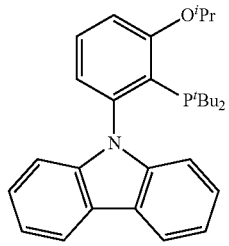
(1-9)

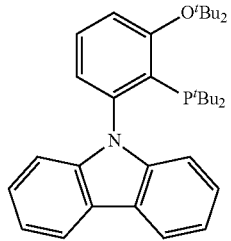
(1-10)

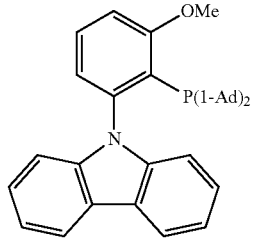
(1-11)

(1-12) 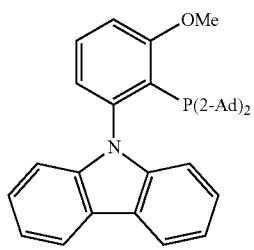
(1-13) 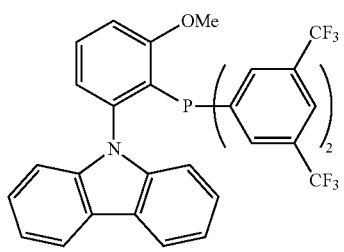
(1-14) 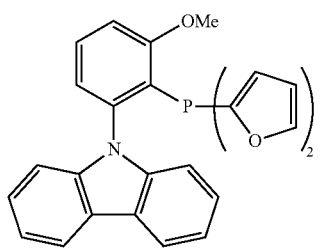
(1-15) 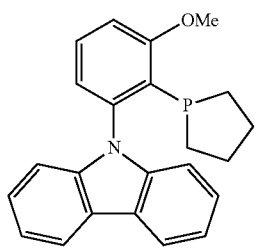
(1-16) 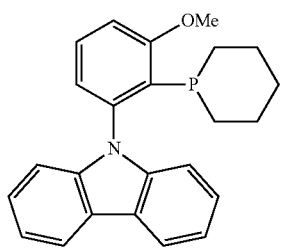
(1-17) 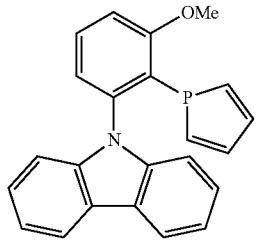
(1-18) 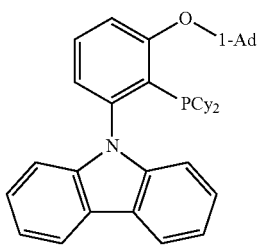
(1-19) 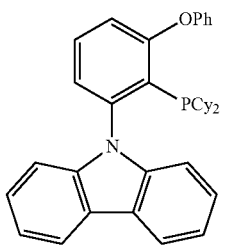
(1-20) 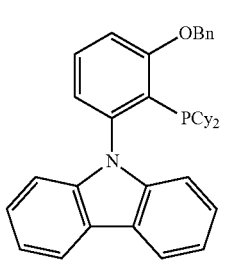
(1-21) 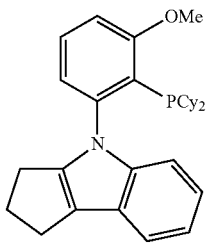
(1-22) 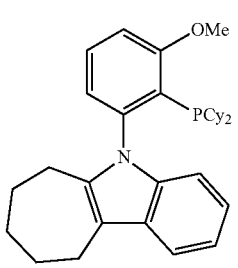
(1-23) 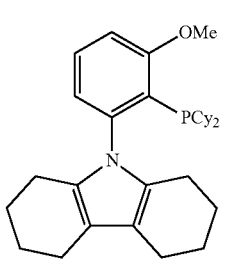

-continued (1-24)
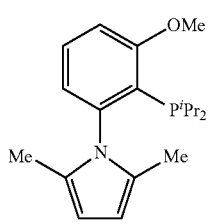

(1-25)
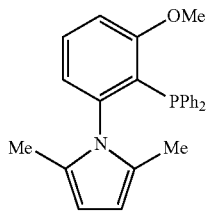

(1-26)
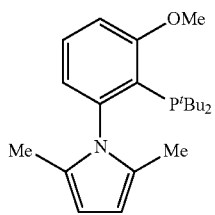

(1-27)
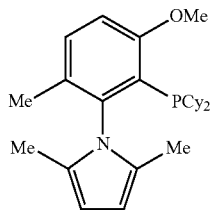

(1-28)
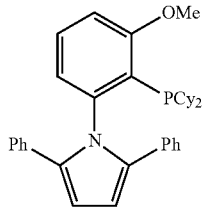

Phosphorus compound (1) of the present invention can be easily produced by combining, as appropriate, known organic synthesis reactions. Although the present invention is not limited to the following examples at all, phosphorus compound (1) of the present invention can be easily synthesized by, for example, deprotonating an N-arylazole represented by general formula (4) (hereinafter, referred to as N-arylazole (4)):

(4)
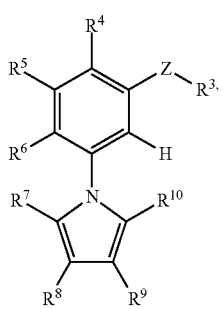

wherein $R^3$ to $R^{10}$, N, and Z are the same as those in general formula (1), and H represents a hydrogen atom with an organometallic reagent such as n-butyllithium, followed by a reaction with a phosphorus compound represented by general formula (5) (hereinafter, referred to as phosphorus compound (5)):

$$X\!-\!P(Y)R^1R^2 \qquad (5)$$

wherein $R^1$, $R^2$, P, and Y are the same as those in general formula (1), and X represents an alkoxy group or a halogeno group (reaction formula 1).

Reaction Formula 1

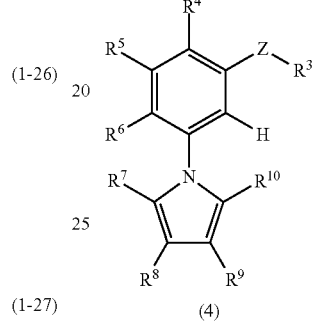

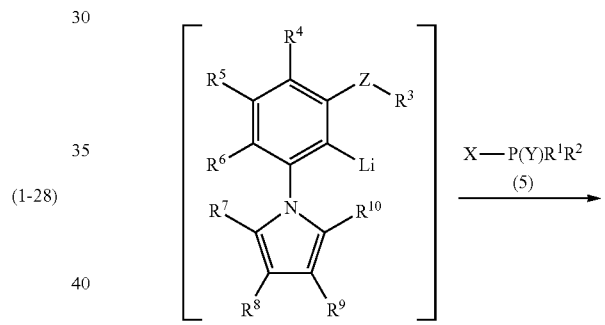

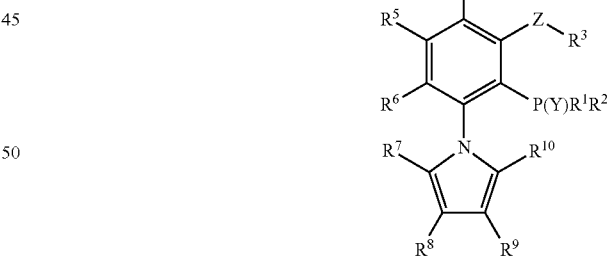

Moreover, N-arylazole (4), which serve as a reactant in this reaction, can be easily synthesized by, for example, 1) dehydration condensation of an arylamine with a 1,4-diketone (route 1 in reaction formula 2), 2) a reaction of a 3-chlorophenol or a 3-chlorothiophenol with $R^3$—X' ($R^3$ is the same as that in general formula (1), and X' represents a halogeno group or a sulfonyloxy group), followed by a coupling reaction with an NH-azole represented by general formula (6) (hereinafter, referred to as NH-azole (6):

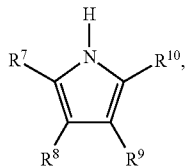

wherein $R^7$ to $R^{10}$ are the same as those in general formula (1), and H represents a hydrogen atom) (route 2 in reaction formula 2), or 3) a coupling reaction of a 3-bromochlorobenzene with NH-azole (6), followed by another coupling reaction with $R^3$—ZH ($R^3$ and Z are the same as those in general formula (1), and H represents a hydrogen atom) (route 3 in reaction formula 2). By selecting a suitable route from these different reaction routes, an extremely wide variety of $R^1$ to $R^{10}$ can be easily introduced into phosphorus compound (1) of the present invention.

Reaction Formula 2

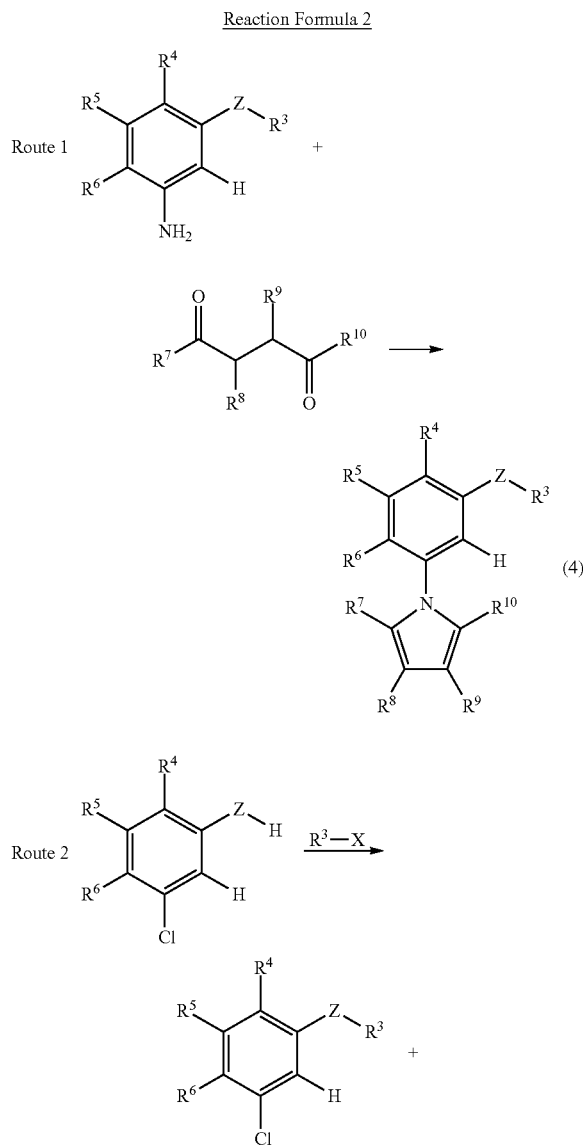

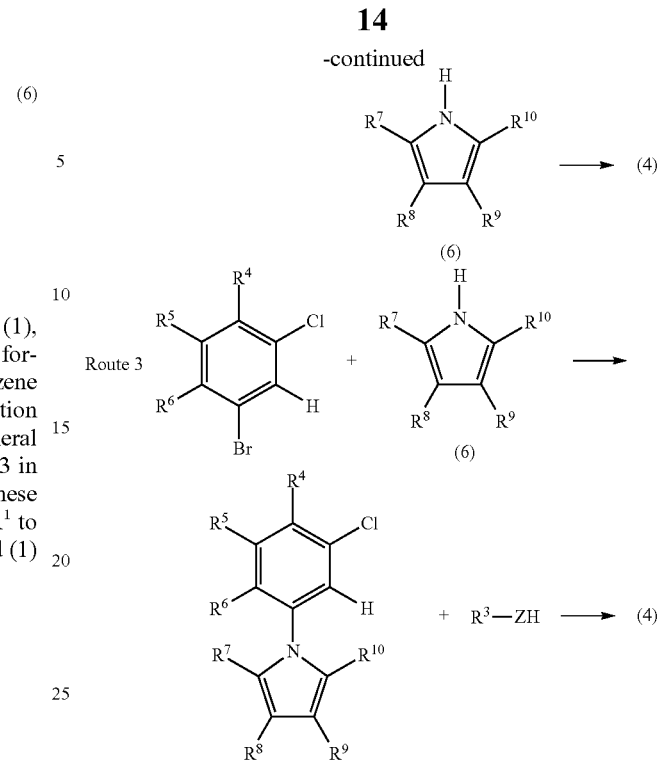

Next, complex (3) of the present invention will be described in further detail. The complex (3) of the present invention is obtained by the coordination of phosphorus compound (1) of the present invention to a transition metal compound. The transition metal compound is not particularly limited, as long as phosphorus compound (1) of the present invention can coordinate to the transition metal compound. From the viewpoint of catalytic action in organic synthesis reactions, preferred examples of the transition metal compound include compounds of iron, cobalt, nickel, copper, ruthenium, rhodium, palladium, silver, osmium, iridium, platinum, gold, and the like, and more preferred examples thereof include palladium compounds. Preferred transition metal compounds are described more specifically.

Examples of the iron compounds include zerovalent, divalent, and trivalent iron compounds, and specific examples thereof include pentacarbonyliron(0), nonacarbonyldiiron(0), iron(II) fluoride, iron(II) chloride, iron(II) chloride tetrahydrate, iron(II) bromide, iron(II) iodide, iron(II) sulfate monohydrate, iron(II) sulfate heptahydrate, iron(II) perchlorate hexahydrate, iron(II) tetrafluoroborate hexahydrate, iron(II) acetate, ammonium iron(II) sulfate hexahydrate, iron(II) acetylacetonate, iron(III) fluoride, iron(III) fluoride trihydrate, iron(III) chloride, iron(III) chloride hexahydrate, iron(III) bromide, iron(III) sulfate n-hydrate, iron(III) nitrate non-ahydrate, iron(III) perchlorate n-hydrate, iron(III) phosphate n-hydrate, iron(III) acetylacetonate, iron(III) trifluoroacetylacetonate, and the like.

Examples of the cobalt compounds include divalent and trivalent cobalt compounds, and specific examples thereof include cobalt(II) fluoride, cobalt(II) fluoride tetrahydrate, cobalt(II) chloride, cobalt(II) chloride dihydrate, cobalt(II) chloride hexahydrate, cobalt(II) bromide, cobalt(II) bromide dihydrate, cobalt(II) iodide, cobalt(II) sulfate monohydrate, cobalt(II) sulfate heptahydrate, cobalt nitrate (II) hexahydrate, cobalt(II) perchlorate hexahydrate, cobalt(II) tetrafluoroborate hexahydrate, cobalt(II) acetate, cobalt(II) acetate tetrahydrate, cobalt(II) cyanide dihydrate, cobalt(II) acetylacetonate, cobalt(II) acetylacetonate dihydrate, cobalt(II) hexafluoroacetylacetonate hydrate, cobalt(III) fluoride, cobalt(III) acetylacetonate, and the like.

Examples of the nickel compounds include zerovalent and divalent nickel compounds, and specific examples thereof include bis(1,5-cyclooctadiene)nickel(0), tetrakis(triphenylphosphine)nickel(0), bis(triphenylphosphine)dichloronickel(II), nickel(II) fluoride, nickel(II) chloride, nickel(II) chloride monohydrate, nickel(II) chloride hexahydrate, nickel(II) bromide, nickel(II) bromide trihydrate, nickel(II) iodide, nickel(II) trifluoromethanesulfonate, nickel(II) sulfate, nickel(II) sulfate hexahydrate, nickel(II) sulfate heptahydrate, nickel(II) nitrate hexahydrate, nickel(II) perchlorate hexahydrate, nickel(II) oxalate dihydrate, nickel(II) acetate tetrahydrate, nickel(II) acetylacetonate, nickel(II) hexafluoroacetylacetonate hydrate, nickel(II) hydroxide, and the like.

Examples of the copper compounds include monovalent and divalent copper compounds, and specific examples thereof include copper(I) oxide, copper(I) chloride, copper(I) bromide, copper(I) iodide, copper(I) trifluoromethanesulfonate benzene complex, copper(I) acetate, copper(I) cyanide, tetrakis(acetonitrile)copper(I) tetrafluoroborate, tetrakis(acetonitrile)copper(I) hexafluorophosphate, copper(II) oxide, copper(II) fluoride, copper(II) fluoride dihydrate, copper(II) chloride, copper(II) chloride dihydrate, copper(II) bromide, copper(II) trifluoromethanesulfonate, copper(II) sulfate, copper(II) sulfate pentahydrate, copper(II) nitrate trihydrate, copper(II) perchlorate hexahydrate, copper(II) tetrafluoroborate hexahydrate, copper(II) trifluoroacetate, copper(II) acetate, copper(II) acetate monohydrate, copper(II) acetylacetonate, copper(II) hexafluoroacetylacetonate hydrate, and the like.

Examples of the ruthenium compounds include divalent and trivalent ruthenium compounds, and specific examples thereof include dichloro(p-cymene)ruthenium(II) dimer, dichloro(mesitylene)ruthenium(II) dimer, dichloro(hexamethylbenzene)ruthenium(II) dimer, diiodo(p-cymene)ruthenium(II) dimer, dichloro(1,5-cyclooctadiene)ruthenium(II) polymer, dichlorotris(triphenylphosphine) ruthenium(II), tris(acetonitrile)cyclopentadienylruthenium(II) hexafluorophosphate, ruthenium(III) chloride, ruthenium(III) chloride trihydrate, ruthenium(III) chloride n-hydrate, ruthenium(III) iodide, ruthenium(III) iodide hydrate, ruthenium(III) acetylacetonate, and the like.

Examples of the rhodium compounds include monovalent, divalent, and trivalent rhodium compounds, and specific examples thereof include chloro(1,5-hexadiene)rhodium(I) dimer, chloro(1,5-cyclooctadiene)rhodium(I) dimer, chlorobis(cyclooctene) rhodium(I) dimer, bis(1,5-cyclooctadiene) rhodium(I) trifluoromethanesulfonate, bis(1,5-cyclooctadiene)rhodium(I) hexafluoroantimonate, bis(1,5-cyclooctadiene)rhodium(I) tetrafluoroborate, bis(norbornadiene)rhodium(I) trifluoromethanesulfonate, (acetylacetonato)bis(ethylene)rhodium(I), (acetylacetonato) (1,5-cyclooctadiene) rhodium(I), (acetylacetonato) (norbornadiene) rhodium(I), bis(acetonitrile) (1,5-cyclooctadiene) rhodium(I) tetrafluoroborate, bis(1,5-cyclooctadiene) rhodium(I) tetrakis[bis(3,5-trifluoromethyl)phenyl]borate, tetrakis(triphenylphosphine)rhodium(I) hydride, (acetylacetonato)dicarbonylrhodium(I), rhodium(III) chloride, rhodium(III) chloride trihydrate, rhodium(III) nitrate n-hydrate, tetrakis(μ-trifluoroacetato)dirhodium(II), tetrakis(μ-acetato) dirhodium(II), tetrakis(μ-acetato)dirhodium(II) dihydrate, tetrakis(μ-trimethylacetato)dirhodium(II), tetrakis(μ-octanoato)dirhodium(II), tetrakis(triphenylacetato)dirhodium(II), rhodium(III) acetylacetonate, and the like.

Examples of the palladium compounds include zerovalent, monovalent, and divalent palladium compounds, and specific examples thereof include bis(dibenzylideneacetone)palladium(0), tris(dibenzylideneacetone)dipalladium (0), tris (dibenzylideneacetone)dipalladium(0) chloroform complex, tetrakis(triphenylphosphine)palladium(0), bis(acetonitrile) dichloropalladium(II), bis(acetonitrile)dibromopalladium (II), bis(benzonitrile)dichloropalladium(II), bis(benzonitrile)dibromopalladium(II), dichloro(1,5-cyclooctadiene) palladium(II), bis(triphenylphosphine)dichloropalladium (II), (n-allyl)palladium(II) chloride dimer, (n-methallyl) palladium(II) chloride dimer, (r-cinnamyl)palladium(II) chloride dimer, palladium(II) chloride, palladium(II) bromide, palladium(II) iodide, palladium(II) sulfate, palladium (II) nitrate dihydrate, palladium(II) trifluoroacetate, palladium(II) acetate, palladium(II) propionate, palladium(II) pivalate, palladium(II) cyanide, palladium(II) acetylacetonate, palladium(II) hexafluoroacetylacetonate, tetrakis(acetonitrile)palladium(II) tetrafluoroborate, sodium tetrachloropalladate(II), potassium tetrachloropalladate(II), and the like. Preferred specific examples thereof include tris(dibenzylideneacetone)dipalladium(0), bis(acetonitrile)palladium (II) dichloride, palladium(II) acetate, (n-allyl)palladium(II) chloride dimer, (π-cinnamyl)palladium(II) chloride dimer, and the like, and a more preferred specific example thereof is (π-allyl)palladium(II) chloride dimer.

Examples of the silver compounds include monovalent and divalent silver compounds, and specific examples thereof include silver(I) oxide, silver(I) fluoride, silver(I) chloride, silver(I) bromide, silver(I) trifluoromethanesulfonate, silver (I) methanesulfonate, silver(I) p-toluenesulfonate, silver(I) sulfate, silver(I) nitrate, silver(I) perchlorate, silver(I) perchlorate monohydrate, silver(I) tetrafluoroborate, silver(I) hexafluorophosphate, silver(I) trifluoroacetate, silver(I) acetate, silver(I) benzoate, silver(I) carbonate, silver(I) nitrite, silver(I) cyanate, silver(I) acetylacetonate, silver(II) fluoride, silver(II) picolinate, and the like.

Examples of the osmium compounds include trivalent osmium compounds, and specific examples thereof include osmium(III) chloride, osmium(III) chloride trihydrate, and the like.

Examples of the iridium compounds include monovalent and trivalent iridium compounds, and specific examples thereof include chloro(1,5-cyclooctadiene)iridium(I) dimer, (1,5-cyclooctadiene)(methoxy)iridium(I) dimer, bis(cyclooctadiene)iridium(I) tetrakis[3,5-bis(trifluoromethyl) phenyl]borate, bis(1,5-cyclooctadiene)iridium(I) tetrafluoroborate, (1,5-cyclooctadiene)(hexafluoroacetylacetonato) iridium(I), (acetylacetonato) (1,5-cyclooctadiene)iridium(I), (acetylacetonato)dicarbonyliridium(I), iridium(III) chloride, iridium(III) chloride hydrate, iridium(III) acetylacetonate, and the like.

Examples of the platinum compound include divalent and tetravalent platinum compounds, and specific examples thereof include platinum(II) chloride, platinum(II) bromide, platinum(II) iodide, platinum(II) cyanide, platinum(II) acetylacetonate, potassium tetrachloroplatinate(II), dichloro(1,5-cyclooctadiene)platinum(II), cis-bis(acetonitrile)dichloroplatinum(II), trans-bis(acetonitrile)dichloroplatinum(II), cis-bis(benzonitrile)dichloroplatinum(II), platinum(IV) chloride, potassium hexachloroplatinate(IV), and the like.

Examples of the gold compounds include monovalent and trivalent gold compounds, and specific examples thereof include gold(I) chloride, gold(I) iodide, gold(I) cyanide, gold (III) chloride, gold(III) chloride dihydrate, gold(III) bromide, chloroauric acid(III) tetrahydrate, potassium chloroaurate (III), and the like.

Although the present invention is not limited to the following examples at all, preferred specific examples of complex (3) of the present invention include compounds (3-1) to (3-21) shown below and the like, and particularly preferred specific examples thereof include compounds (3-1) to (3-7) and the like.
(3-1)
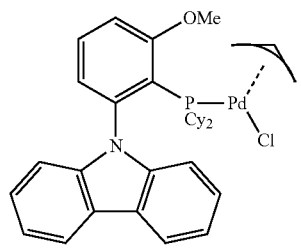
(3-2)
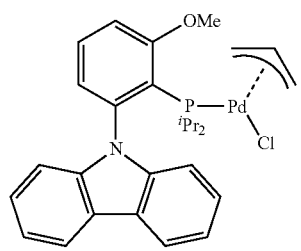
(3-3)
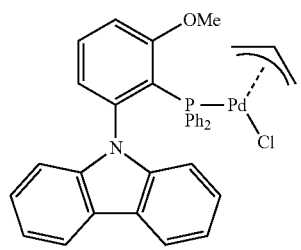
(3-4)
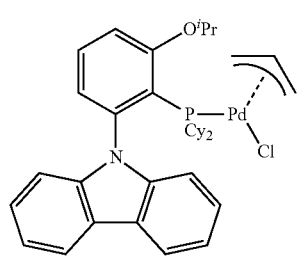
(3-5)
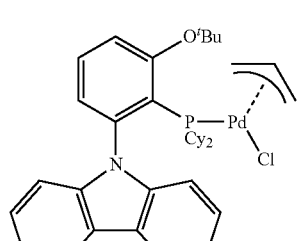
-continued
(3-6)
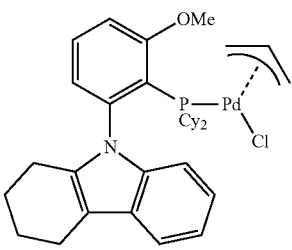
(3-7)
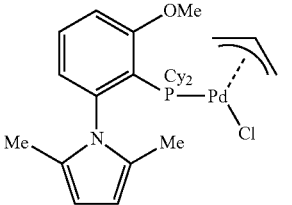
(3-8)
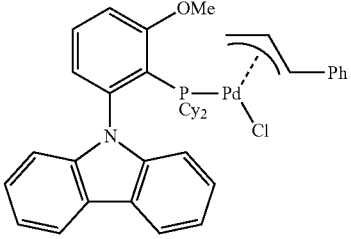
(3-9)
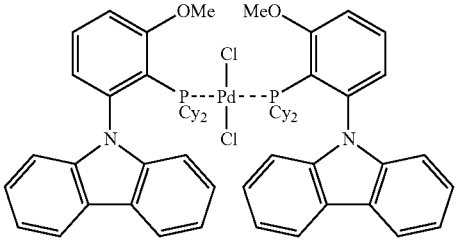
(3-10)
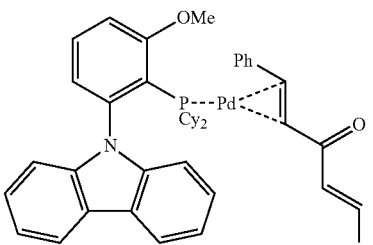
(3-11)
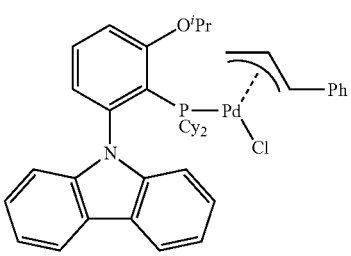

-continued (3-12)
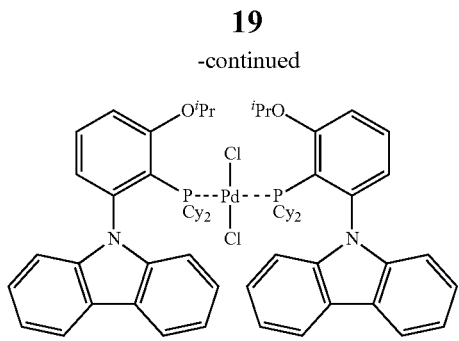

(3-13)
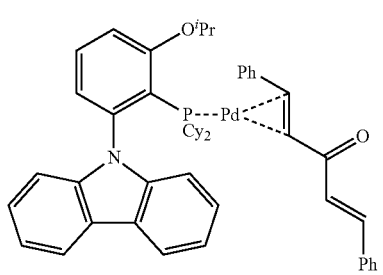

(3-14)
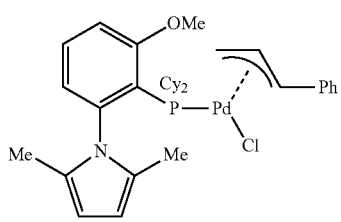

(3-15)
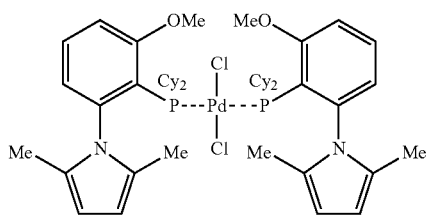

(3-16)
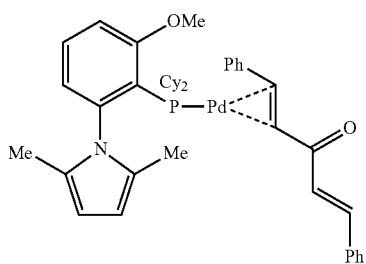

(3-17)
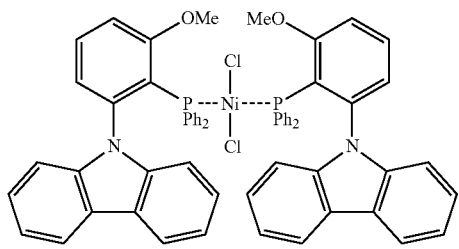

-continued (3-18)

(3-19)
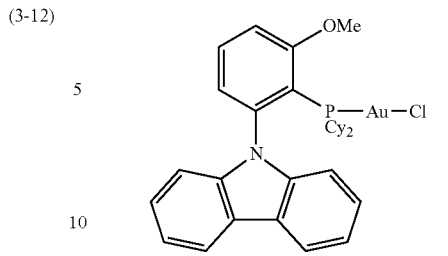

(3-20)
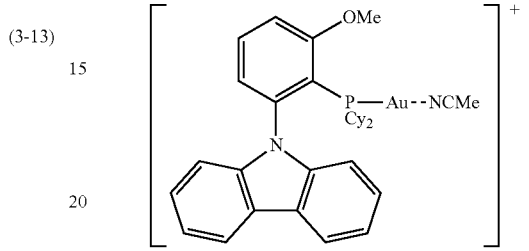

(3-21)
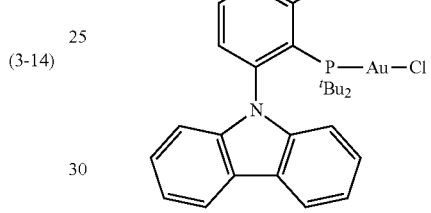

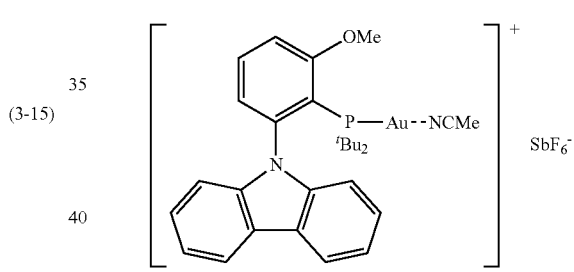

In production of complex (3) of the present invention, it is desirable that a solvent be coexistent. The solvent is not particularly limited, unless the coordinating behavior of phosphorus compound (1) of the present invention to the transition metal compound is inhibited. If necessary, an acid or a base may further be coexistent, and the production may be conducted under an inert gas atmosphere of nitrogen, argon, or the like. If necessary, the thus obtained complex (3) of the present invention can be subjected to post treatment, purification, and isolation. Examples of methods for the post treatment include washing of a reaction solution, extraction of a product, filtration of precipitates, removal of a solvent by distillation, crystallization by addition of a solvent, and the like. One of these post treatments may be conducted alone, or any ones of these post treatments may be conducted in combination. Examples of methods for the purification and the isolation include decolorization with an adsorbent such as activated carbon or silica gel, column chromatography, recrystallization, sublimation, and the like. One of these methods may be conducted alone, or any ones of these methods may be conducted in combination. When complex (3) of the present invention is used as a catalyst in an organic synthesis reaction, the reaction solution containing complex (3) of the present invention may be directly used as a catalyst solution, or, if necessary, may be subjected to any of the above-described post treatments, purification, and isolation before use. One of such complexes (3) may be used alone, or an appropriate combination of two or more thereof may be used. It is also possible to use complex (3) of the present invention in combination with phosphorus compound (1) of the present invention.

Phosphorus compound (1) of the present invention is useful as a ligand for catalytic organic synthesis reactions, and complex (3) of the present invention is useful as a catalyst for organic synthesis reactions. These reactions are not particularly limited, and specifically include oxidation reactions, reduction reactions, hydrogenation reactions, dehydrogenation reactions, hydrogen transfer reactions, addition reactions, conjugate addition reactions, cyclization reactions, functional group conversion reactions, isomerization reactions, rearrangement reactions, polymerization reactions, bond cleavage reactions, bond formation reactions, homo-coupling reactions, cross-coupling reactions, and the like. Cross-coupling reactions are preferable. The cross-coupling reactions are not particularly limited, either, and specifically include the Kochi-Fürstner coupling reaction, the Kumada-Tamao-Corriu coupling reaction, the Mizoroki-Heck reaction, the Murahashi coupling reaction, the Sonogashira-Hagihara coupling reaction, the Negishi coupling reaction, the Migita-Kosugi-Stille coupling reaction, the Suzuki-Miyaura coupling reaction, the Hiyama coupling reaction, the Buchwald-Hartwig coupling reaction, α-arylation reactions of carbonyl compounds, decarboxylative coupling reactions between (hetero)aryl (pseudo)halides and carboxylic acids, coupling reactions between (hetero)aryl (pseudo)halides and hydrocarbons involving carbon-hydrogen bond cleavage, borylation reactions of (hetero)aryl (pseudo)halides, cyanation reactions of (hetero)aryl (pseudo)halides, phosphination reactions of (hetero)aryl (pseudo)halides, fluorination reactions of (hetero)aryl (pseudo)halides, trifluoromethylation reactions of (hetero)aryl (pseudo)halides, and the like, and preferred specific examples thereof include the Suzuki-Miyaura coupling reaction, the Buchwald-Hartwig coupling reaction, and the like.

EXAMPLES

Hereinafter, phosphorus compound (1) of the present invention and complex (3) of the present invention will be described in detail based on Reference Examples, Examples, and Comparative Examples. However, the present invention is not limited to these Reference Examples, Examples, and Comparative Examples at all. In Reference Examples, Examples, and Comparative Examples, the following apparatuses were used to determine physical properties.
1) Proton Nuclear Magnetic Resonance Spectroscopy (hereinafter, abbreviated as $^1$H NMR): Varian Mercury plus 300 (manufactured by Varian, Inc.)
Internal Standard Substance: tetramethylsilane
2) Carbon 13 Nuclear Magnetic Resonance Spectroscopy (hereinafter, abbreviated as $^{13}$C NMR): Varian Mercury plus 300 (manufactured by Varian, Inc.)
Internal Standard Substance: the residual non-deuterated solvent in the deuterated solvent
3) Phosphorus 31 Nuclear Magnetic Resonance Spectroscopy (hereinafter, abbreviated as $^{31}$P NMR): Varian Mercury plus 300 (manufactured by Varian, Inc.)
External Standard Substance: phosphoric acid
4) Gas Chromatography (hereinafter, abbreviated as GC): Gas Chromatograph (Model GC-2010 Plus manufactured by Shimadzu Corporation)
Column: InertCap 1 (manufactured by GL Sciences Inc.), Initial
Temperature: 100° C., Temperature Ramp Rate: 10° C./minute, Final
Temperature: 250° C., Measurement Time: 30 minutes.

Note that each of the reactants, the reagents, the solvents, and the like was added under a nitrogen stream, and each reaction was conducted under a nitrogen atmosphere. In addition, post treatment and purification were conducted in air, unless otherwise noted.

Reference Example 1

Synthesis of N-(2-dicyclohexylphosphinophenyl) carbazole (Structural Formula (2-1)) (Reaction Formula 3)

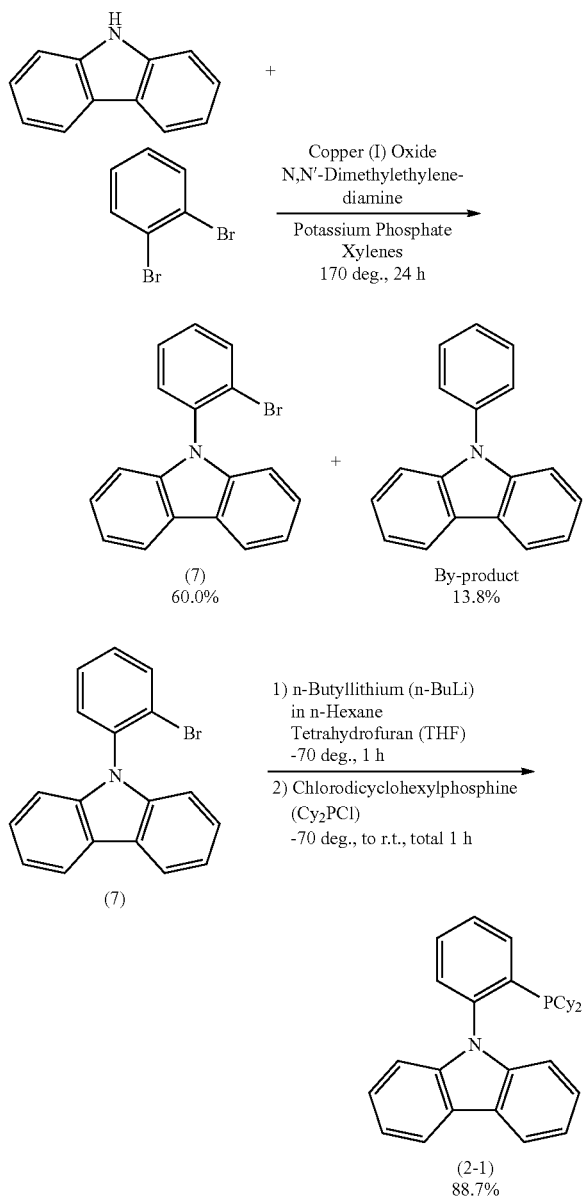

First Step: Synthesis of N-(2-bromophenyl)carbazole (Structural Formula (7))

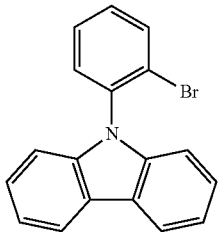

(7)

(Setting-Up and Reaction) To a 500 mL four-necked round-bottomed flask, a three-way stopcock, a mechanical stirrer, a condenser, and a thermometer were attached, and the inside was purged with nitrogen. To this flask, carbazole (19.4 g, 116.3 mmol, 1.0 eq.), 1,2-dibromobenzene (54.8 g, 232.6 mmol, 2.0 eq.), xylenes (120 mL), copper(I) oxide (3.3 g, 23.3 mmol, 0.2 eq.), N,N'-dimethylethylenediamine (5.0 mL, 46.5 mmol, 0.4 eq.), and potassium phosphate (54.3 g, 255.9 mmol, 2.2 eq.) were sequentially added, and the obtained suspension was stirred at 170° C. for 24 hours. Reaction conversion: 80.2%. Note that no improvement in conversion was observed, even when the reaction time was extended further.

(Post Treatment and Purification) After the reaction mixture had been cooled to room temperature, toluene and a 28% aqueous ammonia solution were added to the mixture. The mixture was transferred to a separating funnel, shaken and allowed to stand, and the layers were separated. The organic layer was washed five times with a 28% aqueous ammonia solution (each time the washing was repeated, the blue color of the aqueous layer faded), once with water, and three times with a 1 N aqueous hydrochloric acid solution (hardly soluble black tar was formed in each of the organic layer and the aqueous layer). The organic layer was concentrated, and the obtained residue was purified by conducting silica gel column chromatography (Eluent: n-hexane/toluene=10/1 to 2/1) three times (because column fractions containing by-products were purified repeatedly) to give 22.5 g of title compound (7) as a pale yellow solid. Isolated Yield: 60.0%. Note that 3.9 g of a by-product, N-phenylcarbazole, was obtained as a colorless solid. Isolated Yield: 13.8%.

$^1$H NMR (300 MHz, deuterated chloroform (hereinafter, abbreviated as CDCl$_3$)): δ=8.15 (d, J=7.8 Hz, 2H), 7.85 (dd, J=1.5, 8.1 Hz, 1H), 7.56-7.35 (m, 5H), 7.29 (dt, J=0.9, 6.9 Hz, 2H), 7.06 (d, J=8.1 Hz, 2H).

$^{13}$C NMR (75 MHz, CDCl$_3$): δ=140.8, 136.7, 134.2, 131.1, 130.1, 128.8, 125.9, 123.8, 123.2, 120.3, 120.0, 110.0.

By-product (N-phenylcarbazole):

$^1$H NMR (300 MHz, CDCl$_3$): δ=7.25-7.33 (m, 2H), 7.38-7.50 (m, 5H), 7.53-7.64 (m, 4H), 8.16 (dt, J=7.8, 0.9 Hz, 2H).

$^{13}$C NMR (75 MHz, CDCl$_3$): δ=109.7, 119.9, 120.3, 123.3, 125.9, 127.1, 127.4, 129.8, 137.7, 140.9.

Second Step: Synthesis of N-(2-dicyclohexylphosphinophenyl)carbazole (Structural Formula (2-1))

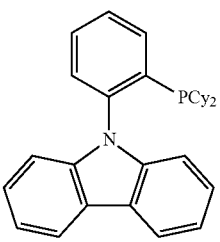

(2-1)

(Setting-Up and Reaction) To a 200 mL four-necked round-bottomed flask, a three-way stopcock, a Teflon®-coated magnetic stirring bar, a 20 mL dropping funnel, and a thermometer were attached, and the inside was purged with nitrogen. To this flask, N-(2-bromophenyl)carbazole (7) (8.8 g, 27.3 mmol, 1.0 eq.) obtained in the first step and anhydrous tetrahydrofuran (hereinafter, abbreviated as THF) (54.6 mL) were sequentially added, and the obtained reactant solution was cooled to −70° C. by use of a dry ice/acetone bath. Subsequently, a n-butyllithium (hereinafter, abbreviated as n-BuLi)/n-hexane solution (1.60 mol/L, 17.9 mL, 28.6 mmol, 1.05 eq.) was placed in the dropping funnel, and added dropwise over 15 minutes, while the reactant solution was being stirred, and the inside temperature was being kept at −50° C. or below. Then, the dropping funnel was rinsed with anhydrous n-hexane (1 mL). The obtained cream-colored suspension was stirred at −70° C. for 1 hour. Then, an anhydrous THF (14 mL) solution of chlorodicyclohexylphosphine (hereinafter, abbreviated as Cy$_2$PCl) (7.0 g, 30.1 mmol, 1.1 eq.) was placed in the dropping funnel, and added dropwise over 15 minutes, while the suspension was being stirred, and the inside temperature was being kept at −50° C. or below (the suspension was dissolved rapidly). After completion of the dropwise addition, the dry ice/acetone bath was taken out, and the temperature of the reaction solution was raised to room temperature over 30 minutes, followed by stirring for further 30 minutes.

(Post Treatment and Purification) After the reaction solution had been concentrated under reduced pressure, toluene and an aqueous solution of sodium hydrogen carbonate (2.3 g, approximately 1 eq.) were added to the residue. The mixture was transferred to a separating funnel, shaken and allowed to stand, and the layers were separated (Aqueous Layer 1: pH=9). Then, the organic layer was further washed with water (Aqueous Layer 2: pH=7). The solvent was distilled off from the organic layer under reduced pressure, and toluene and silica gel (0.7 g) were added to the obtained light brown residue. The mixture was stirred at room temperature for 10 minutes and filtered by use of diatomaceous earth, and the residue was washed with toluene. The filtrate was concentrated, until crystals were precipitated. Then, methanol was added, and the obtained white suspension was filtered. The product obtained by the filtration was washed with methanol, and then dried under reduced pressure to give 10.6 g of title compound (2-1) as a colorless powder. Isolated Yield: 88.3%.

$^1$H NMR (300 MHz, CDCl$_3$): δ=8.12 (d, J=7.5 Hz, 2H), 7.76 (dt, J=1.5, 4.8 Hz, 1H), 7.57-7.47 (m, 2H), 7.38-7.28 (m, 3H), 7.23 (dt, J=0.9, 6.9 Hz, 2H), 7.02 (d, J=8.1 Hz, 2H), 1.85-1.38 (m, 12H), 1.22-0.90 (m, 10H). $^{31}$P NMR (121 MHz, CDCl$_3$): δ=−14.5.

Reference Example 2

Synthesis of N-(2-di-tert-butylphosphinophenyl) carbazole (Structural Formula (2-2)) (Reaction Formula 4)

Reaction Formula 4

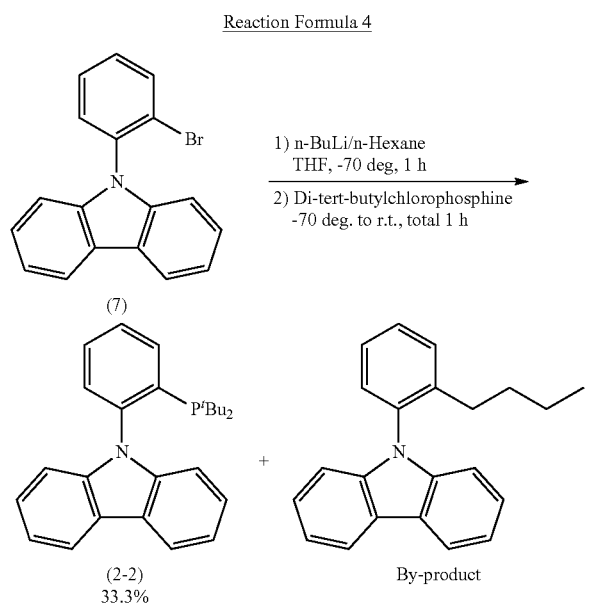

(Setting-Up and Reaction) To a 100 mL four-necked round-bottomed flask, a three-way stopcock, a Teflon®-coated magnetic stirring bar, a 10 mL dropping funnel, and a thermometer were attached, and the inside was purged with nitrogen. To this flask, N-(2-bromophenyl)carbazole (7) (2.5 g, 7.76 mmol, 1.0 eq.) obtained in the first step of Reference Example 1 and anhydrous THF (15.0 mL) were sequentially added, and the obtained reactant solution was cooled to −70° C. by use of a dry ice/acetone bath. Subsequently, a n-BuLi/n-hexane solution (1.60 mol/L, 5.1 mL, 8.16 mmol, 1.05 eq.) was placed in the dropping funnel, and was added dropwise over 10 minutes, while the reactant solution was being stirred, and the inside temperature was being kept at −50° C. or below. Then, the dropping funnel was rinsed with anhydrous n-hexane (1 mL). The obtained cream-colored suspension was stirred at −70° C. for 1 hour. Then, di-tert-butylchlorophosphine (1.63 mL, 8.58 mmol, 1.1 eq.) and anhydrous THF (3 mL) were sequentially placed in the dropping funnel, and were added dropwise over 5 minutes, while the suspension was being stirred (no heat generation was observed, and the suspension was not dissolved). After completion of the dropwise addition, the dry ice/acetone bath was removed, and the temperature was allowed to rise. The suspension started to dissolve at an inside temperature of −40° C. After that, the temperature of the reaction solution was raised to room temperature over 30 minutes, followed by stirring for further 30 minutes.

(Post Treatment and Purification) After the reaction solution had been concentrated under reduced pressure, toluene and an aqueous solution of sodium hydrogen carbonate (0.7 g, approximately 1 eq.) were added to the residue. The mixture was transferred to a separating funnel, shaken and allowed to stand, and the layers were separated (Aqueous Layer 1: pH=10). The organic layer was further washed with water (Aqueous Layer 2: pH=7). The solvent was distilled off from the organic layer under reduced pressure, and the obtained residue was purified by silica gel column chromatography (Eluent: n-hexane/toluene=10/1 to toluene) to give 1.0 g of title compound (2-2) as a colorless powder. Isolated Yield: 33.3%. Note that the major by-product was N-(2-n-butylphenyl) carbazole.

$^1$H NMR (300 MHz, CDCl$_3$): δ=8.12 (dd, J=0.6, 7.5 Hz, 2H), 8.09-8.03 (m, 1H), 7.57-7.47 (m, 2H), 7.36-7.26 (m, 3H), 7.22 (dd, J=0.9, 7.2 Hz, 2H), 7.04 (d, J=8.1 Hz, 2H), 1.10 (d, J=12.0 Hz, 18H) $^{31}$P NMR (121 MHz, CDCl$_3$): δ=18.5.

By-Product (N-(2-n-butylphenyl)carbazole):

$^1$H NMR (300 MHz, CDCl$_3$): δ=8.15 (d, J=7.2 Hz, 2H), 7.54-7.21 (m, 8H), 7.04 (d, J=8.1 Hz, 2H), 2.32 (t, J=7.5 Hz, 2H), 1.29 (quin, J=7.5 Hz, 2H), 0.98 (sext, J=7.5 Hz, 2H), 0.56 (t, J=7.5 Hz, 3H).

$^{13}$C NMR (75 MHz, CDCl$_3$): δ=142.2, 141.7, 135.7, 130.5, 129.6, 128.8, 127.3, 125.8, 123.0, 120.2, 119.4, 109.9, 32.4, 30.8, 22.1, 13.5.

As can be seen from Reference Examples 1 and 2, an extremely low-temperature condition is necessary for the synthesis of conventional compound (2), because n-butylation by the by-produced 1-bromobutane occurs as a side reaction. Even the extremely low-temperature condition failed to suppress the side reaction, depending on the structure of phosphorus compound (5) reacted. To avoid the side reaction, it is necessary to replace the n-BuLi with 2 equivalents of tert-butyllithium. However, this reagent is extremely unstable and highly pyrophoric, and moreover, unless the temperature is extremely low, decomposes the solvent THF. Accordingly, this reagent is unsuitable for industrial use anyway. In addition, the synthesis of N-(2-bromophenyl)carbazole (7), which is an intermediate of conventional compound (2), has problems associated with the Ullmann reaction which requires high temperature and long time, the post treatment which requires a large amount of ammonia water, and the by-production of N-phenylcarbazole which is difficult to separate even by silica gel column chromatography. To avoid the Ullmann reaction, we attempted the synthesis of (7) by various alternative methods such as the Buchwald-Hartwig coupling reaction, but failed. Accordingly, we have found that it is extremely difficult to synthesize a large amount of conventional compound (2) easily at low costs.

Example 1

Synthesis of N-(2-dicyclohexylphosphino-3-methoxyphenyl)carbazole (Structural Formula (1-1)) (Reaction Formula 5)

Reaction Formula 5

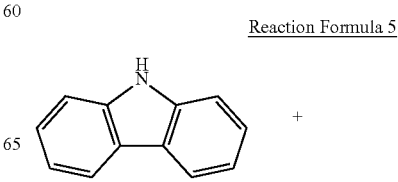

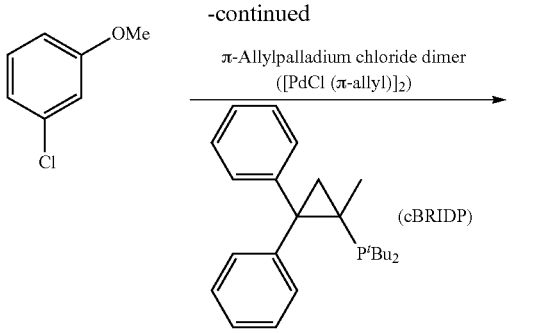

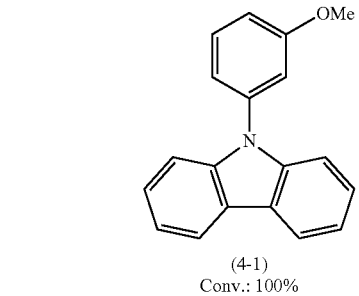

(4-1)
Conv.: 100%

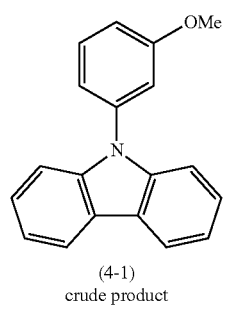

(4-1)
crude product

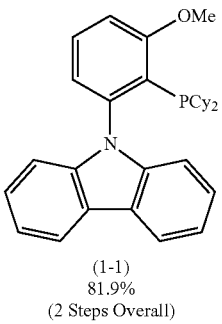

(1-1)
81.9%
(2 Steps Overall)

First Step: Synthesis of
N-(3-methoxyphenyl)carbazole (Structural Formula (4-1))

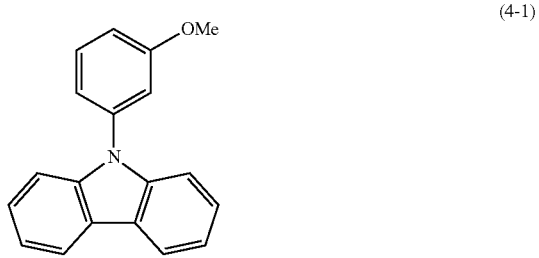 [SMILES: COc1cccc(-n2c3ccccc3c3ccccc32)c1]

(4-1)

(Setting-Up and Reaction) To a 100 mL two-necked round-bottomed flask, (n-allyl)palladium(II) chloride dimer (hereinafter, abbreviated as [PdCl(π-allyl)]$_2$) (32.1 mg, 0.05 mol %) and di-tert-butyl(2,2-diphenyl-1-methyl-1-cyclopropyl)phosphine (hereinafter, abbreviated as cBRIDP) (123.6 mg, 0.2 mol %) were added. Then, a three-way stopcock was attached to the flask, and the inside was purged with nitrogen. Subsequently, anhydrous THF (8.0 mL) was added, and the mixture was shaken at room temperature for 1 minute and further diluted with anhydrous xylenes (30 mL). Thus, a mixture solution of (π-allyl) [di-tert-butyl(2,2-diphenyl-1-methyl-1-cyclopropyl)phosphine]palladium(II) chloride (0.1 mol %) and cBRIDP (0.1 mol %) was prepared as a pale yellow liquid (38 mL) (hereinafter, this liquid is abbreviated as catalyst solution). On the other hand, a three-way stopcock, a Teflon®-coated magnetic stirring bar, a condenser, a 100 mL dropping funnel, and a thermometer were attached to a 500 mL four-necked round-bottomed flask, and the inside was purged with nitrogen. To this flask, carbazole (29.9 g, 178.8 mmol, 1.02 eq.), anhydrous xylenes (150 mL), and anhydrous THF (15 mL) were sequentially added, and the obtained reactant suspension was cooled to 5° C. by use of an ice-water bath. Subsequently, a methylmagnesium chloride (hereinafter, abbreviated as MeMgCl)/THF solution (3.02 mol/L, 58.6 mL, 177.1 mmol, 1.01 eq.) was placed in the dropping funnel, and added dropwise over 20 minutes, while the reactant suspension was being stirred, and the inside temperature was being kept at 20° C. or below (the suspension was rapidly dissolved with the formation of bubbles). Then, the dropping funnel was rinsed with anhydrous xylenes (30 mL). Subsequently, 3-chloroanisole (25.0 g, 175.3 mmol, 1.0 eq.) and the catalyst solution (38 mL) were sequentially added to the reaction solution, and then stirring was started under reflux (approximately 110° C.). As the reaction proceeded, magnesium chloride was precipitated. A GC analysis was conducted at a time point where the reaction was carried out for 0.5 hours to check the progress of the reaction. The GC analysis showed that 3-chloroanisole was completely consumed.

(Post Treatment) After the obtained suspension had been cooled to room temperature, water (90 mL) and ammonium chloride (4.7 g, approximately 0.5 eq.) were added. The mixture was filtered by use of diatomaceous earth, the aqueous layer was separated (Aqueous Layer 1: pH=9), and the organic layer was further washed with water (90 mL) (Aqueous Layer 2: pH=7). The organic layer was concentrated under reduced pressure, and toluene (180 mL) and silica gel (1.5 g) were added to the obtained brown viscous liquid. The mixture was stirred at room temperature for 10 minutes and filtered by use of diatomaceous earth, and the residue was washed with toluene. The filtrate was concentrated under reduced pressure, and toluene was added to adjust the total amount to 191.7 g. Thus, a toluene solution of a crude product of title compound (4-1) (approximately 25% by weight, counted as 0.914 mmol/g) was obtained. This solution was used in the second step without any further purification. Note that the structure of title compound (4-1) was identified by purifying a portion of this solution by silica gel column chromatography (Eluent: n-hexane/toluene=2/1), and subjecting the purified product to NMR analyses.

$^1$H NMR (300 MHz, CDCl$_3$): δ=8.14 (d, J=7.8 Hz, 2H), 7.50 (t, J=8.1 Hz, 1H), 7.46-7.36 (m, 4H), 7.28 (ddd, J=1.8, 6.6, 8.1 Hz, 2H), 7.16 (ddd, J=0.6, 1.8, 7.8 Hz, 1H), 7.10 (t, J=0.9 Hz, 1H), 7.05 (ddd, J=0.9, 2.7, 8.4 Hz, 1H), 3.85 (s, 3H).

$^{13}$C NMR (75 MHz, CDCl$_3$): δ=160.8, 140.8, 138.8, 130.5, 125.9, 123.3, 120.3, 119.9, 119.3, 113.2, 112.6, 109.9, 55.5.

Second Step: Synthesis of N-(2-dicyclohexylphosphino-3-methoxyphenyl)carbazole (Structural Formula (1-1))

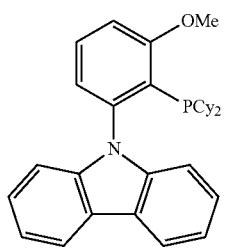

(1-1)

(Setting-Up and Reaction) To a 100 mL four-necked round-bottomed flask, the toluene solution of the crude product of N-(3-methoxyphenyl)carbazole (4-1) obtained in the first step (counted as 0.914 mmol/g, 21.3 g) was added, and toluene was distilled off under reduced pressure to weigh out the crude product of N-(3-methoxyphenyl) carbazole (4-1) (counted as 19.5 mmol, 1.0 eq.) (since N-(3-methoxyphenyl) carbazole (4-1) was a high-viscosity liquid, and was difficult to exactly weigh out, N-(3-methoxyphenyl)carbazole (4-1) was prepared as the toluene solution, and toluene was distilled off immediately before the operation of the second step; this operation was also intended for drying the reactant by azeotropic dehydration). To this flask, a three-way stopcock, a Teflon®-coated magnetic stirring bar, a dropping funnel, and a thermometer were attached, and then the inside of flask was purged with nitrogen. Then, anhydrous THF (40 mL) was added, and the obtained reactant solution was cooled to 5° C. by use of an ice-water bath. Subsequently, a n-BuLi/n-hexane solution (1.60 mol/L, 12.8 mL, 20.5 mmol, 1.05 eq.) was placed in the dropping funnel, and added dropwise over 10 minutes, while the reactant solution was being stirred, and the inside temperature was being kept at 10° C. or below. Then, the dropping funnel was rinsed with anhydrous n-hexane (1 mL). The obtained reddish-orange suspension was stirred at 5° C. for 1 hour. Then, an anhydrous THF (10 mL) solution of Cy$_2$PCl (5.0 g, 21.5 mmol, 1.1 eq.) was placed in the dropping funnel, and added dropwise over 15 minutes, while the suspension was being stirred, and the inside temperature was being kept at 10° C. or below (the suspension was dissolved rapidly). After completion of the dropwise addition, the reaction solution was stirred at 5° C. for 30 minutes.

(Post Treatment and Purification) After the obtained suspension had been concentrated under reduced pressure, toluene and an aqueous solution of sodium hydrogen carbonate (1.6 g, approximately 1 eq.) were added to the residue. The mixture was transferred to a separating funnel, shaken and allowed to stand, and the layers were separated (Aqueous Layer 1: pH=9). Then, the organic layer was further washed with water (Aqueous Layer 2: pH=7). After methanol (5 mL) had been added to the organic layer, the solvents were distilled off under reduced pressure, and toluene and silica gel (500 mg) were added to the residue. The mixture was stirred at 40° C. for 10 minutes and filtered by use of diatomaceous earth, and the residue was washed with toluene. The filtrate was concentrated, until crystals were precipitated. Then, methanol was added, and the obtained white suspension was filtered. The product obtained by the filtration was washed with methanol, and then dried under reduced pressure to give 7.5 g of title compound (1-1) as a colorless powder. Two Steps Overall Isolated Yield: 81.9%.

$^1$H NMR (300 MHz, CDCl$_3$): δ=8.12 (d, J=7.8 Hz, 2H), 7.47 (t, J=8.1 Hz, 1H), 7.36 (ddd, J=1.2, 7.5, 8.4 Hz, 2H), 7.27-7.17 (m, 2H), 7.04-6.94 (m, 3H), 6.89 (ddd, J=0.9, 3.6, 7.8 Hz, 1H), 3.93 (s, 3H), 2.30-2.15 (m, 2H), 1.70-1.50 (m, 8H), 1.50-1.35 (m, 2H), 1.25-0.75 (m, 10H).

$^{31}$P NMR (121 MHz, CDCl$_3$): δ=−3.9.

Example 2

Synthesis of N-(2-diisopropylphosphino-3-methoxyphenyl)carbazole (Structural Formula (1-2)) (Reaction Formula 6)

Reaction Formula 6

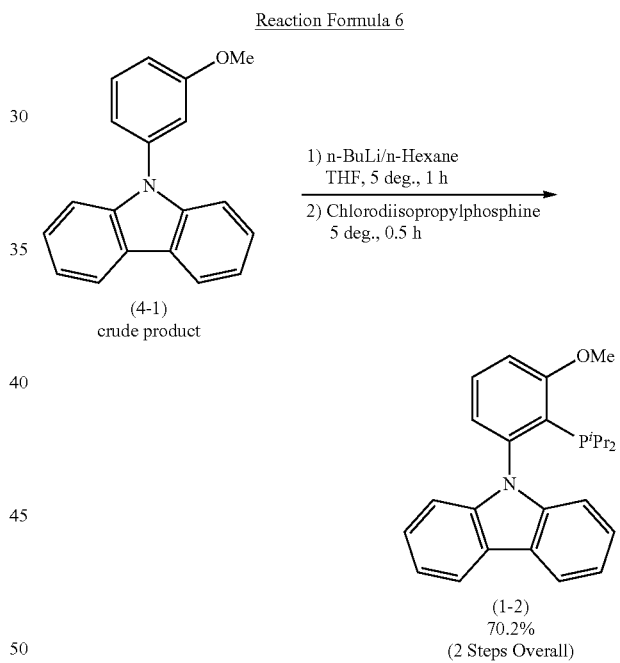

Title compound (1-2) (5.0 g) was obtained as a colorless powder by the same procedure as in the second step of Example 1, except that the reaction was conducted by use of the toluene solution of the crude product of N-(3-methoxyphenyl) carbazole (4-1) in an amount equivalent to 18.3 mmol, that chlorodiisopropylphosphine was used instead of Cy$_2$PCl, and further that the product was isolated and purified by crystallization from toluene/methanol. Two Steps Overall Isolated Yield: 70.2%.

$^1$H NMR (300 MHz, CDCl$_3$): δ=8.12 (d, J=7.8 Hz, 2H), 7.49 (t, J=8.4 Hz, 1H), 7.38-7.29 (m, 2H), 7.27-7.18 (m, 2H), 7.05-6.98 (m, 3H), 6.92 (dd, J=3.6, 7.8 Hz, 1H), 3.19 (s, 3H), 2.56-2.39 (m, 2H), 0.93-0.79.

$^{31}$P NMR (121 MHz, CDCl$_3$): δ=6.7.

Example 3

Synthesis of N-(2-diphenylphosphino-3-methoxyphenyl)carbazole (Structural Formula (1-3)) (Reaction Formula 7)

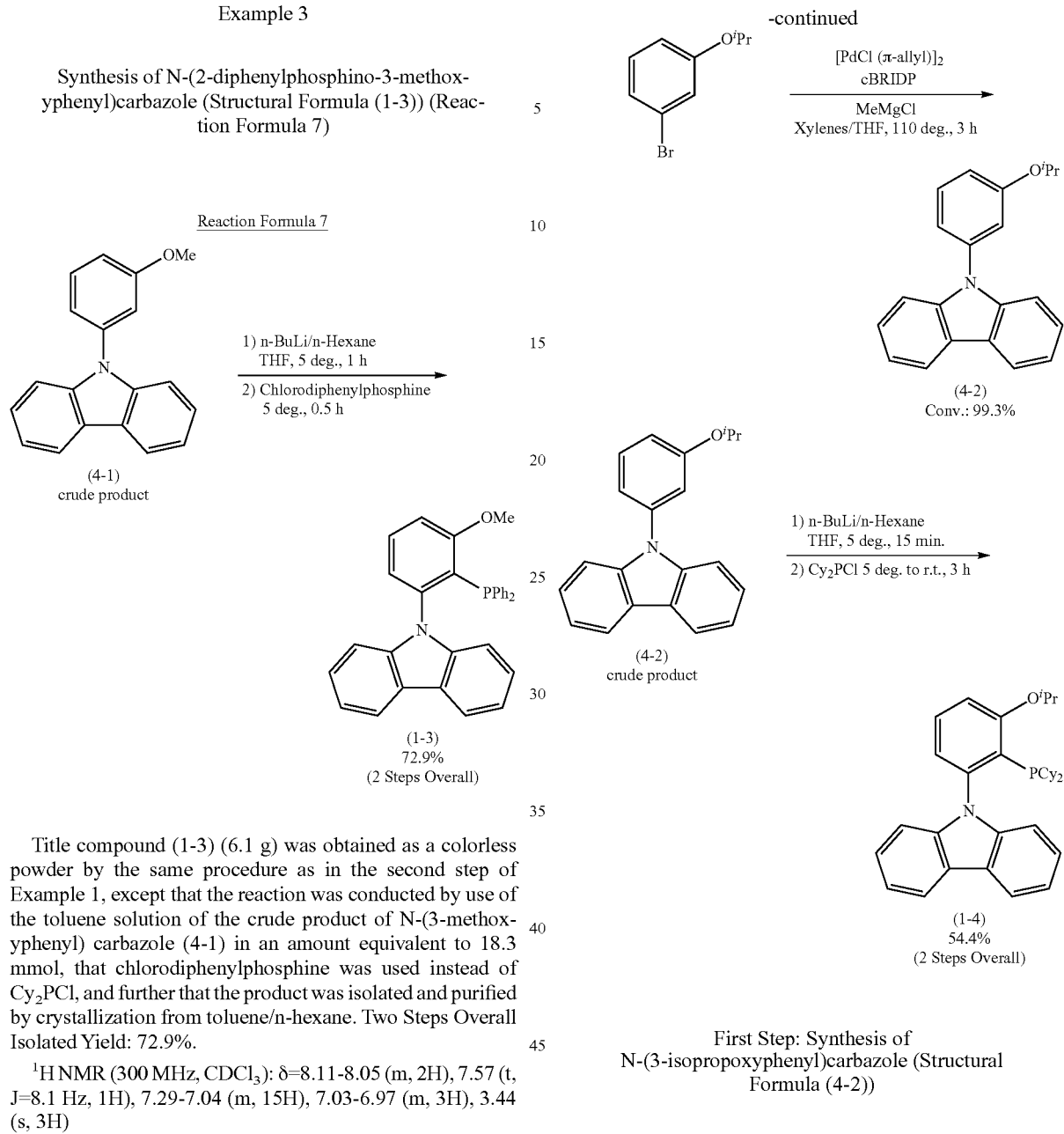

Title compound (1-3) (6.1 g) was obtained as a colorless powder by the same procedure as in the second step of Example 1, except that the reaction was conducted by use of the toluene solution of the crude product of N-(3-methoxyphenyl) carbazole (4-1) in an amount equivalent to 18.3 mmol, that chlorodiphenylphosphine was used instead of Cy$_2$PCl, and further that the product was isolated and purified by crystallization from toluene/n-hexane. Two Steps Overall Isolated Yield: 72.9%.

$^1$H NMR (300 MHz, CDCl$_3$): δ=8.11-8.05 (m, 2H), 7.57 (t, J=8.1 Hz, 1H), 7.29-7.04 (m, 15H), 7.03-6.97 (m, 3H), 3.44 (s, 3H)

$^{31}$P NMR (121 MHz, CDCl$_3$): δ=−16.4.

Example 4

Synthesis of N-(2-dicyclohexylphosphino-3-isopropoxyphenyl)carbazole (Structural Formula (1-4)) (Reaction Formula 8)

Reaction Formula 8

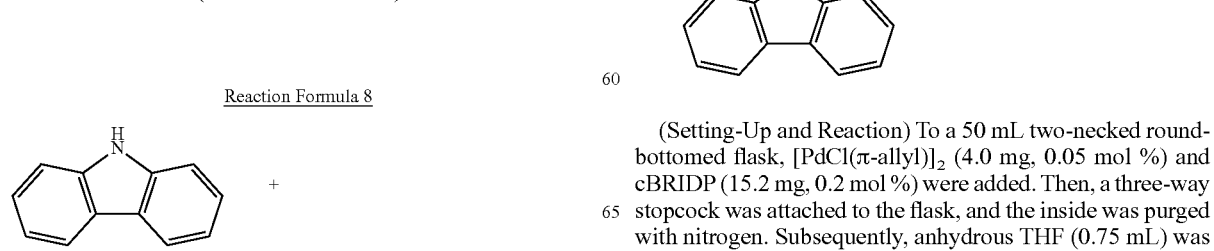

First Step: Synthesis of N-(3-isopropoxyphenyl)carbazole (Structural Formula (4-2))

(Setting-Up and Reaction) To a 50 mL two-necked round-bottomed flask, [PdCl(π-allyl)]$_2$ (4.0 mg, 0.05 mol %) and cBRIDP (15.2 mg, 0.2 mol %) were added. Then, a three-way stopcock was attached to the flask, and the inside was purged with nitrogen. Subsequently, anhydrous THF (0.75 mL) was added, and the mixture was shaken at room temperature for 1 minute. Further, anhydrous xylenes (5 mL) were added to prepare a catalyst solution (5.75 mL). On the other hand, to a 100 mL four-necked round-bottomed flask, a three-way stopcock, a Teflon®-coated magnetic stirring bar, a condenser, a 10 mL dropping funnel, and a thermometer were attached, and the inside was purged with nitrogen. To this flask, carbazole (4.71 g, 22.1 mmol, 1.03 eq.), anhydrous xylenes (15 mL), and anhydrous THF (1.5 mL) were sequentially added, and the obtained reactant suspension was cooled to 5° C. by use of an ice-water bath. Subsequently, a MeMgCl/THF solution (3.02 mol/L, 7.3 mL, 22.1 mmol, 1.02 eq.) was placed in the dropping funnel and added dropwise, while the reactant suspension was being stirred, and the inside temperature was being kept at 20° C. or below. Then, the dropping funnel was rinsed with anhydrous xylenes (3 mL). Subsequently, 3-bromoisopropoxybenzene (4.62 g, 21.5 mmol, 1.0 eq.) and the catalyst solution (5.75 mL) were sequentially added to the reaction solution, and then the inlet was rinsed with anhydrous xylenes (2 mL). The reaction mixture was stirred for 3 hours under reflux (approximately 110° C.). Reaction Conversion: 99.3% (GC).

(Post Treatment) After the obtained suspension had been cooled to room temperature, a 10% by weight aqueous ammonium chloride solution (30 mL) was added. The mixture was transferred to a separating funnel, shaken and allowed to stand, and the layers were separated. The aqueous layer was extracted twice with toluene (30 mL). The organic layers were combined, washed twice with water (10 mL), dried over anhydrous sodium sulfate, and then filtered. The filtrate was concentrated to give 7.07 g of a crude product of title compound (4-2) as a brown viscous liquid. The entire amount of the crude product was used in the second step without any further purification.

Second Step: Synthesis of N-(2-dicyclohexylphosphino-3-isopropoxyphenyl)carbazole (Structural Formula (1-4))

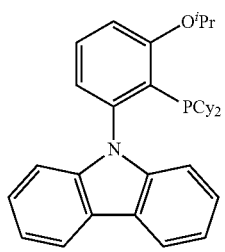

(1-4)

(Setting-Up and Reaction) To a 50 mL four-necked round-bottomed flask, a three-way stopcock, a Teflon®-coated magnetic stirring bar, a dropping funnel, and a thermometer were attached, and the inside was purged with nitrogen. To this flask, an anhydrous THF (21.5 mL) solution of the crude product of N-(3-isopropoxyphenyl)carbazole (4-2) obtained in the first step (7.07 g, counted as 21.5 mmol, 1.0 eq.) was added, and cooled to 5° C. by use of an ice-water bath. A n-BuLi/n-hexane solution (1.60 mol/L, 13.4 mL, 21.5 mmol, 1.0 eq.) was placed in the dropping funnel, and was added dropwise over 10 minutes, while the reactant solution was being stirred, and the inside temperature was being kept at 10° C. or below. Then, the obtained brown reaction solution was stirred at 5° C. for 15 minutes. Subsequently, an anhydrous THF (10 mL) solution of $Cy_2PCl$ (5.0 g, 21.5 mmol, 1.0 eq.) was placed in the dropping funnel, and added dropwise over 15 minutes, while the reaction liquid was being stirred, and the inside temperature was being kept at 10° C. or below. After completion of the dropwise addition, the reaction solution was stirred at 5° C. for 3 hours.

(Post Treatment and Purification) The reaction solution was concentrated under reduced pressure, diluted with toluene (100 mL), and then washed three times with water (20 mL). The organic layer was dried over anhydrous sodium sulfate and then filtered, and the solvent was distilled off from the filtrate under reduced pressure. After toluene (40 mL) and silica gel (0.5 g) had been added to the obtained residue, the mixture was stirred at room temperature for 10 minutes, and then filtered by use of diatomaceous earth. The residue was washed with toluene. The solvent was distilled off from the filtrate under reduced pressure, and the obtained residue was purified by crystallization (toluene/methanol=1/8) to give 5.8 g of title compound (1-4) as a colorless powder. Two Steps Overall Isolated Yield: 54.4%.

$^1$H NMR (300 MHz, CDCl$_3$): δ=8.12 (d, J=7.8 Hz, 2H), 7.44 (t, J=8.1 Hz, 1H), 7.34 (ddd, J=1.2, 7.2, 8.1 Hz, 2H), 7.26-7.18 (m, 2H), 7.01 (d, J=8.1 Hz, 2H), 6.97 (d, J=8.1 Hz, 1H), 6.84 (dd, J=3.6, 7.8 Hz, 1H), 4.76 (sep, J=6.0 Hz, 1H), 2.38-2.22 (m, 2H), 1.74-1.38 (m, 10H), 1.47 (d, J=6.0 Hz, 6H), 1.28-0.76 (m, 10H)

$^{31}$P NMR (121 MHz, CDCl$_3$): δ=−5.2.

Example 5

Synthesis of N-(2-dicyclohexylphosphino-3-tert-butoxyphenyl)carbazole (Structural Formula (1-5)) (Reaction Formula 9)

Reaction Formula 9

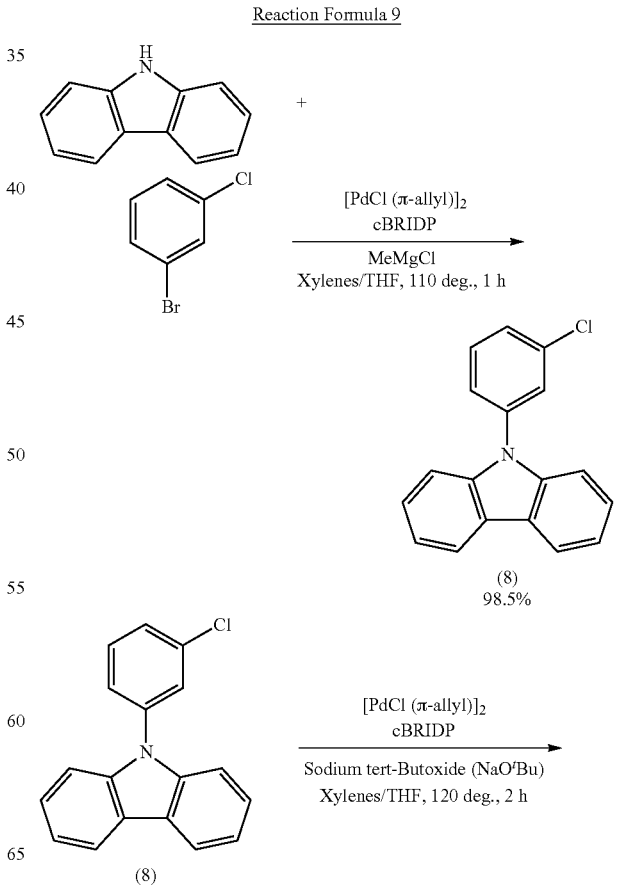

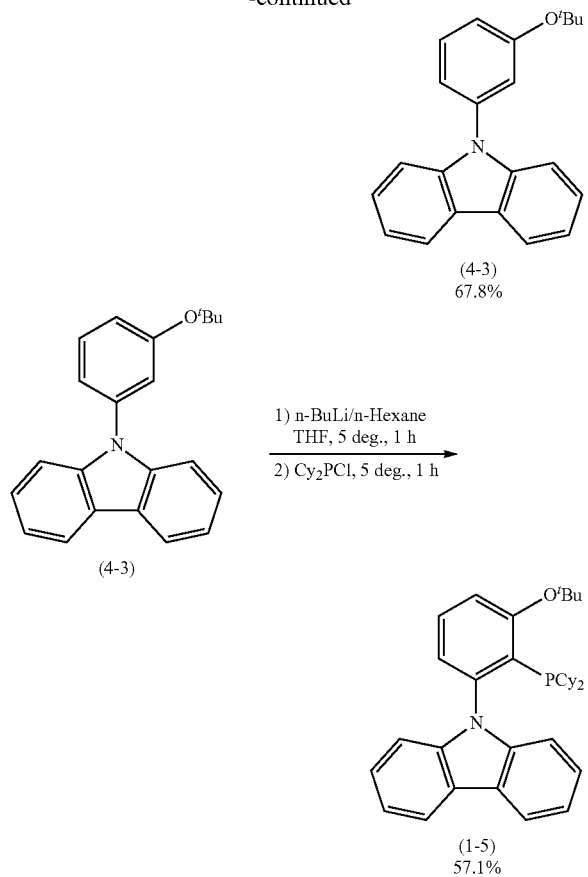

First Step: Synthesis of N-(3-chlorophenyl)carbazole (Structural Formula (8))

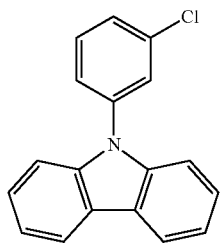

(Setting-Up and Reaction) To a 50 mL two-necked round-bottomed flask, [PdCl(π-allyl)]2 (10.8 mg, 0.05 mol %) and cBRIDP (41.8 mg, 0.2 mol %) were added. A three-way stopcock was attached to the flask, and the inside was purged with nitrogen. Subsequently, anhydrous THF (5 mL) was added, and the mixture was shaken at room temperature for 1 minute and further diluted with anhydrous xylenes (20 mL) to prepare a catalyst solution (25 mL). On the other hand, to a 300 mL four-necked round-bottomed flask, a three-way stopcock, a Teflon®-coated magnetic stirring bar, a condenser, a 50 mL dropping funnel, and a thermometer were attached, and the inside was purged with nitrogen. To this flask, carbazole (20.4 g, 178.8 mmol, 1.03 eq.), anhydrous xylenes (100 mL), and anhydrous THF (10 mL) were sequentially added, and the obtained reactant suspension was cooled to 5° C. by use of an ice-water bath. Subsequently, a MeMgCl/THF solution (3.02 mol/L, 40.0 mL, 120.8 mmol, 1.02 eq.) was placed in the dropping funnel, and added dropwise over 20 minutes, while the reactant suspension was being stirred, and the inside temperature was being kept at 20° C. or below. Then, the dropping funnel was rinsed with anhydrous xylenes (20 mL). Subsequently, 3-bromochlorobenzene (14.0 mL, 118.4 mmol, 1.0 eq.) and the catalyst solution (25 mL) were sequentially added to the reaction solution, and then the mixture was stirred for 1 hour under reflux (approximately 110° C.). Reaction Conversion: >99.9% (GC).

(Post Treatment) After the obtained suspension had been cooled to room temperature, water (60 mL) and ammonium chloride (3.2 g, approximately 0.5 eq.) were added. The mixture was filtered by use of diatomaceous earth, the aqueous layer was separated (Aqueous Layer 1: pH=9), and further the organic layer was washed with water (60 mL) (Aqueous Layer 2: pH=7). The organic layer was concentrated under reduced pressure, and the obtained brown viscous liquid was purified by silica gel column chromatography (Eluent: n-hexane/toluene=4/1 to 2/1) to give 32.4 g of title compound (8) as a colorless viscous liquid. Isolated Yield: 98.5%. For exact measurement of the weight, a toluene solution of title compound (8) (25% by weight, 0.900 mmol/g) was prepared after the purification and used in the second step.

$^1$H NMR (300 MHz, CDCl$_3$): δ=8.13 (dt, J=7.5, 0.9 Hz, 2H), 7.58 (t, J=2.1 Hz, 1H), 7.56-7.38 (m, 8H), 7.35-7.25 (m, 2H).
$^{13}$C NMR (75 MHz, CDCl$_3$): δ=140.5, 140.0, 135.4, 130.8, 127.6, 127.2, 126.1, 125.2, 123.5, 120.4, 120.3, 109.6.

Second Step: Synthesis of N-(3-tert-butoxyphenyl)carbazole (Structural Formula (4-3))

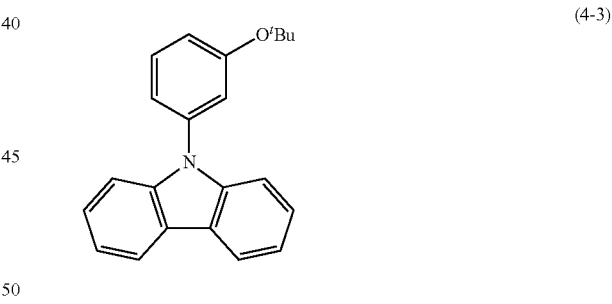

(Setting-Up and Reaction) To a 50 mL two-necked round-bottomed flask, [PdCl(π-allyl)]$_2$ (65.9 mg, 0.5 mol %) and cBRIDP (253.8 mg, 2.0 mol %) were added. A three-way stopcock was attached to the flask, and the inside was purged with nitrogen. Subsequently, anhydrous THF (5 mL) was added, and the mixture was shaken at room temperature for 1 minute to prepare a catalyst solution (5 mL). On the other hand, the toluene solution of N-(3-chlorophenyl)carbazole (8) obtained in the first step (0.900 mmol/g, 40.0 g) was weighed out into a 100 mL four-necked round-bottomed flask, and toluene was distilled off under reduced pressure to weigh out N-(3-chlorophenyl)carbazole (8) (36.0 mmol, 1.0 eq.). To this flask, a three-way stopcock, a Teflon®-coated magnetic stirring bar, a condenser, and a thermometer were attached, and the inside was purged with nitrogen. Subsequently, anhydrous xylenes (50 mL), sodium tert-butoxide (hereinafter, abbreviated as NaO$^t$Bu) (3.8 g, 39.6 mmol, 1.1 eq.), and the catalyst solution (5 mL) were sequentially added, and the reaction solution was stirred for 2 hours under reflux (approximately 120° C.). Reaction Conversion: >99.9% (GC).

(Post Treatment and Purification) After the obtained suspension had been cooled to room temperature, water was added. Then, the mixture was filtered by use of diatomaceous earth, and the residue was washed with toluene. The aqueous layer was separated from the filtrate, and the organic layer was washed with water and then concentrated under reduced pressure. The obtained black viscous liquid was purified by silica gel column chromatography (Eluent: n-hexane/toluene=2/1 to 1/1) to give 7.7 g of title compound (4-3) as a pale yellow viscous liquid. Isolated Yield: 67.8%.

$^1$H NMR (300 MHz, CDCl$_3$): δ=8.13 (dt, J=7.5, 0.9 Hz, 2H), 7.47 (t, J=8.1 Hz, 1H), 7.43-7.36 (m, 4H), 7.32-7.23 (m, 3H), 7.20 (t, J=2.1 Hz, 1H), 7.09 (ddd, J=1.2, 2.4, 8.4 Hz, 1H), 1.41 (s, 9H).

$^{13}$C NMR (75 MHz, CDCl$_3$): δ=156.7, 140.8, 138.1, 129.9, 125.9, 123.3, 123.1, 122.7, 121.9, 120.3, 119.9, 109.8, 79.2, 28.9.

Third Step: Synthesis of N-(2-dicyclohexylphosphino-3-tert-butoxyphenyl)carbazole (Structural Formula (1-5))

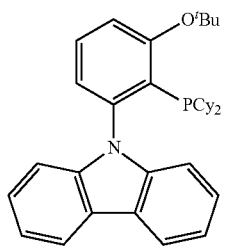

(1-5)

(Setting-Up and Reaction) To a 100 mL four-necked round-bottomed flask, a three-way stopcock, a Teflon®-coated magnetic stirring bar, a 20 mL dropping funnel, and a thermometer were attached, and the inside was purged with nitrogen. To this flask, an anhydrous THF (40 mL) solution of N-(3-tert-butoxyphenyl)carbazole (4-3) (6.2 g, 19.5 mmol, 1.0 eq.) obtained in the second step was added and cooled to 5° C. by use of an ice-water bath. A n-BuLi/n-hexane solution (1.60 mol/L, 12.8 mL, 20.5 mmol, 1.05 eq.) was placed in the dropping funnel, and added dropwise over 10 minutes, while the reactant solution was being stirred, and the inside temperature was being kept at 10° C. or below. Then, the dropping funnel was rinsed with anhydrous n-hexane (1 mL). The obtained black reaction solution was stirred at 5° C. for 1 hour. Then, an anhydrous THF (10 mL) solution of Cy$_2$PCl (5.0 g, 21.5 mmol, 1.1 eq.) was placed in the dropping funnel, and added dropwise over 15 minutes, while the reaction liquid was being stirred, and the inside temperature was being kept at 10° C. or below. After completion of the dropwise addition, the reaction solution was stirred at 5° C. for 1 hour.

(Post Treatment and Purification) After the reaction solution had been concentrated under reduced pressure, toluene and an aqueous solution of sodium hydrogen carbonate (1.6 g, approximately 1 eq.) were added. The mixture was transferred to a separating funnel, shaken and allowed to stand, and the layers were separated. Then, the organic layer was further washed with water and concentrated under reduced pressure. Toluene and silica gel (500 mg) were added to the residue, and the mixture was stirred at room temperature for 10 minutes and filtered by use of diatomaceous earth. The residue was washed with toluene, and the solvent was distilled off from the filtrate under reduced pressure. The obtained residue was purified by crystallization from toluene/acetonitrile to give 5.7 g of title compound (1-5) as a colorless powder. Isolated Yield: 57.1%.

$^1$H NMR (300 MHz, CDCl$_3$): δ=8.11 (d, J=7.5 Hz, 2H), 7.43-7.28 (m, 3H), 7.26-7.12 (m, 3H), 7.01 (d, J=8.1 Hz, 2H), 6.82 (ddd, J=0.9, 3.6, 7.8 Hz, 1H), 2.42-2.24 (m, 2H), 1.78-1.38 (m, 10H), 1.66 (s, 9H), 1.28-0.74 (m, 10H).

$^{31}$P NMR (121 MHz, CDCl$_3$): δ=−5.7.

Example 6

Synthesis of 9-(2-dicyclohexylphosphino-3-methoxyphenyl)-2,3,4,9-tetrahydro-1H-carbazole (Structural Formula (1-6)) (Reaction Formula 10)

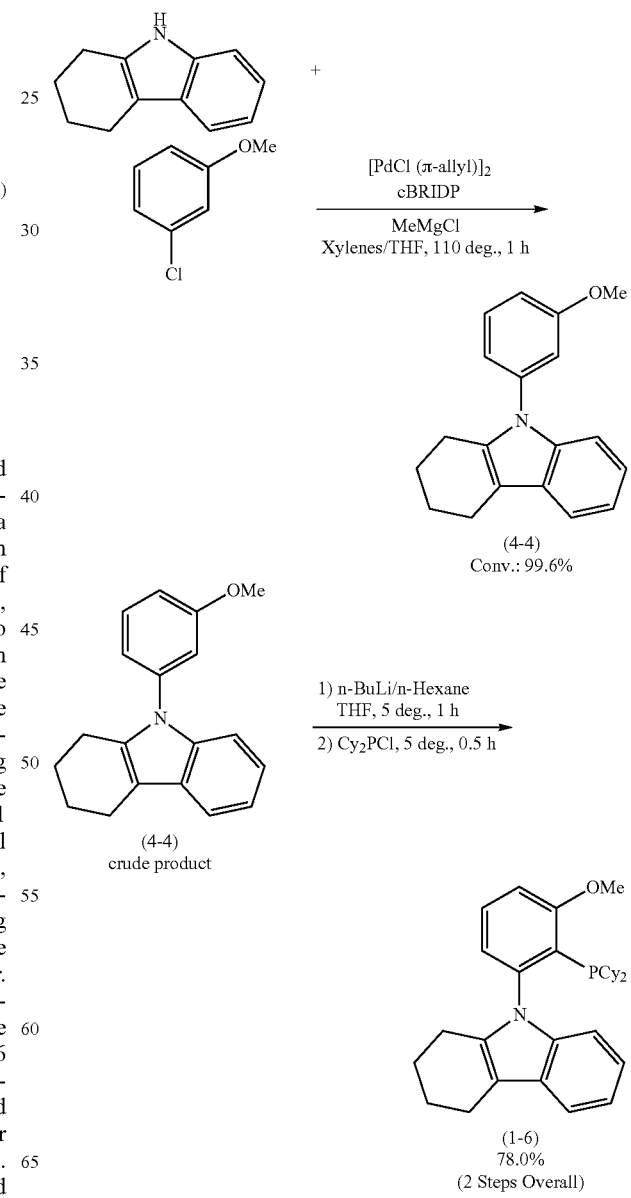

Reaction Formula 10

First Step: Synthesis of 9-(3-methoxyphenyl)-2,3,4,9-tetrahydro-1H-carbazole (Structural Formula (4-4))

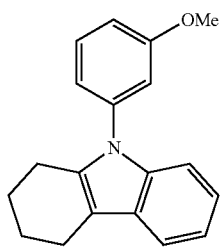

(4-4)

(Setting-Up and Reaction) To a 50 mL two-necked round-bottomed flask, [PdCl(π-allyl)]$_2$ (26.2 mg, 0.05 mol %) and cBRIDP (100.9 mg, 0.2 mol %) were added. A three-way stopcock was attached to the flask, and the inside was purged with nitrogen. Subsequently, anhydrous THF (6.0 mL) was added, and the mixture was shaken at room temperature for 1 minute, and further diluted with anhydrous xylenes (25 mL) to prepare a catalyst solution (31 mL). On the other hand, to a 500 mL four-necked round-bottomed flask, a three-way stopcock, a Teflon®-coated magnetic stirring bar, a condenser, a 100 mL dropping funnel, and a thermometer were attached, and the inside was purged with nitrogen. To this flask, tetrahydrocarbazole (25.0 g, 146.0 mmol, 1.02 eq.), anhydrous xylenes (125 mL), and anhydrous THF (13 mL) were sequentially added, and the obtained reactant suspension was cooled to 5° C. by use of an ice-water bath. Subsequently, a MeMgCl/THF solution (3.02 mol/L, 47.9 mL, 144.5 mmol, 1.01 eq.) was placed in the dropping funnel, and added dropwise over 15 minutes, while the reactant suspension was being stirred, and the inside temperature was being kept at 20° C. or below. Then, the dropping funnel was rinsed with anhydrous xylenes (25 mL). Subsequently, 3-chloroanisole (17.5 mL, 143.1 mmol, 1.0 eq.) and the catalyst solution (31 mL) were sequentially added to the reaction solution, and then the mixture was stirred for 1 hour under reflux (approximately 110° C.). Reaction Conversion: 99.6% (GC).

(Post Treatment) After the obtained suspension had been cooled to room temperature, water (75 mL) and ammonium chloride (3.8 g, approximately 0.5 eq.) were added. The mixture was filtered by use of diatomaceous earth, the aqueous layer was separated, and further the organic layer was washed with water (75 mL). The organic layer was concentrated under reduced pressure, and toluene (150 mL) and silica gel (1.3 g) were added to the obtained brown viscous liquid. The mixture was stirred at room temperature for 10 minutes, and then filtered by use of diatomaceous earth. The residue was washed with toluene. The filtrate was concentrated under reduced pressure, and toluene was added to adjust the total amount to 191.7 g. Thus, a toluene solution of a crude product of title compound (4-4) (approximately 25% by weight, counted as 0.901 mmol/g) was obtained. This solution was used in the second step without any further purification. Note that the structure of title compound (4-4) was identified by purifying a portion of this solution by silica gel column chromatography (Eluent: n-hexane/toluene=1/1) and subjecting the purified product to NMR analyses.

$^1$H NMR (300 MHz, CDCl$_3$): δ=7.54-7.47 (m, 1H), 7.38 (t, J=7.8 Hz, 1H), 7.29-7.21 (m, 1H), 7.15-7.05 (m, 2H), 6.98-6.87 (m, 3H), 3.81 (s, 3H), 2.84-2.74 (m, 2H), 2.66-2.56 (m, 2H), 1.96-1.80 (m, 4H).

$^{13}$C NMR (75 MHz, CDCl$_3$): δ=160.3, 139.1, 137.0, 135.7, 129.9, 127.7, 121.3, 119.5, 119.4, 117.7, 112.8, 112.7, 111.0, 109.9, 55.4, 23.4, 23.3, 23.1, 21.1.

Second Step: Synthesis of 9-(2-dicyclohexylphosphino-3-methoxyphenyl)-2,3,4,9-tetrahydro-1H-carbazole (Structural Formula (1-6))

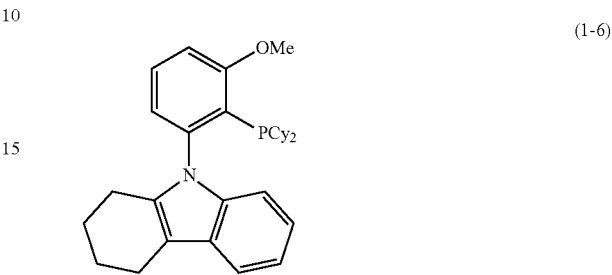

(1-6)

(Setting-Up and Reaction) To a 100 mL four-necked round-bottomed flask, the toluene solution of the crude product of 9-(3-methoxyphenyl)-2,3,4,9-tetrahydro-1H-carbazole (4-4) obtained in the first step (counted as 0.901 mmol/g, 21.6 g) was added, and toluene was distilled off under reduced pressure to weigh out the crude product of 9-(3-methoxyphenyl)-2,3,4,9-tetrahydro-1H-carbazole (4-4) (counted as 19.5 mmol, 1.0 eq.). To this flask, a three-way stopcock, a Teflon®-coated magnetic stirring bar, a dropping funnel, and a thermometer were attached, and then the inside was purged with nitrogen. Anhydrous THF (40 mL) was added, and the obtained reactant solution was cooled to 5° C. by use of an ice-water bath. Subsequently, a n-BuLi/n-hexane solution (1.60 mol/L, 12.8 mL, 20.5 mmol, 1.05 eq.) was placed in the dropping funnel, and added dropwise over 10 minutes, while the reactant solution was being stirred, and the inside temperature was being kept at 10° C. or below. Then, the dropping funnel was rinsed with anhydrous n-hexane (1 mL). The obtained cream-colored suspension was stirred at 5° C. for 1 hour. Then, an anhydrous THF (10 mL) solution of Cy$_2$PCl (5.0 g, 21.5 mmol, 1.1 eq.) was placed in the dropping funnel, and added dropwise over 15 minutes, while the suspension was being stirred, and the inside temperature was being kept at 10° C. or below. After completion of the dropwise addition, the reaction solution was stirred at 5° C. for 30 minutes.

(Post Treatment and Purification) After the reaction solution had been concentrated under reduced pressure, toluene and an aqueous solution of sodium hydrogen carbonate (1.6 g, approximately 1 eq.) were added to the residue. The mixture was transferred to a separating funnel, shaken and allowed to stand, and layers were separated. Then, the organic layer was further washed with water and concentrated under reduced pressure, and toluene and silica gel (500 mg) were added to the residue. The mixture was stirred at room temperature for 10 minutes, and then filtered by use of diatomaceous earth. The residue was washed with toluene, and the filtrate was concentrated. The obtained residue was purified by crystallization (crystals were precipitated from toluene/methanol=1/2, and then methanol was further added) to give 7.2 g of title compound (1-6) as a colorless powder. Two Steps Overall Isolated Yield: 78.0%.

$^1$H NMR (300 MHz, CDCl$_3$): δ=7.51-7.45 (m, 1H), 7.38 (t, J=8.4 Hz, 1H), 7.08-6.96 (m, 2H), 6.93 (d, J=8.4 Hz, 1H), 6.84-6.74 (m, 2H), 3.89 (s, 3H), 2.94-2.70 (m, 2H), 2.65-2.50 (m, 1H), 2.46-2.24 (m, 2H), 2.19-2.04 (m, 1H), 2.00-0.80 (m, 24H) $^{31}$P NMR (121 MHz, CDCl$_3$): δ=−4.7.

Example 7

Synthesis of 1-(2-dicyclohexylphosphino-3-methoxyphenyl)-2,5-dimethylpyrrole (Structural Formula (1-7)) (Reaction Formula 11)

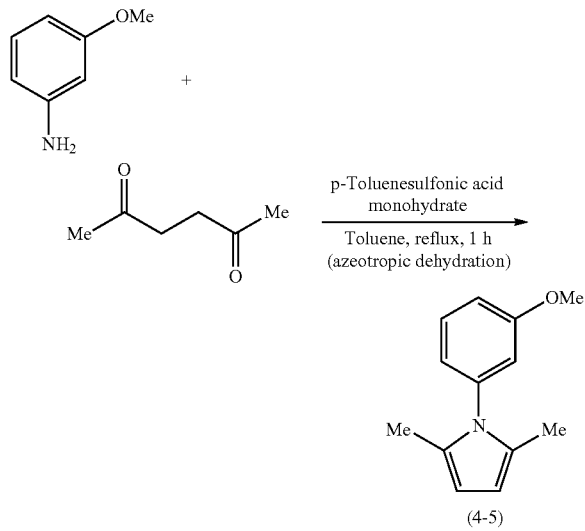
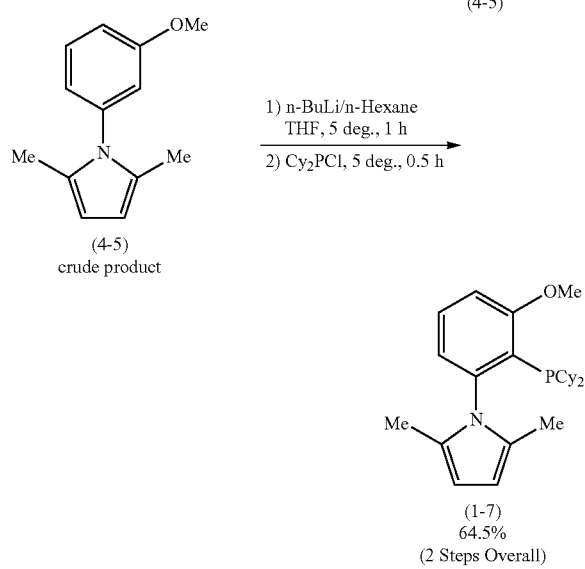

Reaction Formula 11

First Step: Synthesis of 1-(3-methoxyphenyl)-2,5-dimethylpyrrole (Structural Formula (4-5))

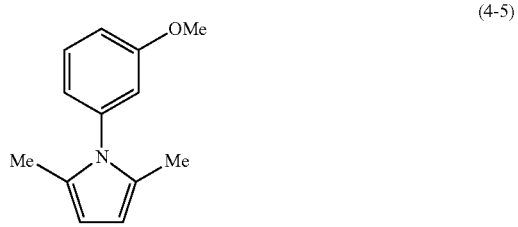 [SMILES: COc1cccc(-n2c(C)ccc2C)c1]

(Setting-Up and Reaction) To a 200 mL four-necked round-bottomed flask, a three-way stopcock, a Teflon®-coated magnetic stirring bar, a Dean-Stark apparatus, a condenser, and a thermometer were attached, and the inside was purged with nitrogen. To this flask, toluene (125 mL), m-anisidine (25.0 g, 203.0 mmol, 1.0 eq.), acetonylacetone (24.5 g, 214.6 mmol, 1.06 eq.), and p-toluenesulfonic acid monohydrate (386 mg, 1.0 mol %) were sequentially added, and the mixture was stirred for 1 hour under reflux, while the by-produced water was removed by azeotropic dehydration.

(Post Treatment) After the reaction solution had been cooled to room temperature, an aqueous sodium hydrogen carbonate solution was added under a nitrogen atmosphere, and the mixture was stirred. After the aqueous layer had been separated, the organic layer was washed twice with water, and then concentrated under reduced pressure. The total amount of the concentrate was adjusted to 163.4 g by dilution with toluene. Thus, a toluene solution of a crude product of title compound (4-5) (approximately 25% by weight, counted as 1.242 mmol/g) was obtained. The thus obtained title compound (4-5) was almost pure, and the structure of title compound (4-5) was identified by concentrating a portion of the toluene solution to dryness, and subjecting the obtained product to NMR analyses.

$^1$H NMR (300 MHz, CDCl$_3$): δ=7.36 (t, J=8.1 Hz, 1H), 6.95 (ddd, J=0.9, 2.4, 8.4 Hz, 1H), 6.81 (ddd, J=0.9, 1.8, 7.8 Hz, 1H), 6.76 (t, J=2.1 Hz, 1H), 5.90 (s, 2H), 3.83 (s, 3H), 2.06 (s, 6H).

$^{13}$C NMR (75 MHz, CDCl$_3$): δ=160.0, 140.1, 129.6, 128.8, 120.5, 113.8, 113.4, 105.6, 55.4, 13.0.

Second Step: Synthesis of 1-(2-dicyclohexylphosphino-3-methoxyphenyl)-2,5-dimethylpyrrole (Structural Formula (1-7))

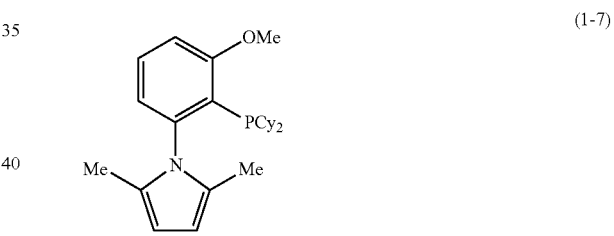

(Setting-Up and Reaction) To a 100 mL four-necked round-bottomed flask, the toluene solution of the crude product of 1-(3-methoxyphenyl)-2,5-dimethylpyrrole (4-5) obtained in the first step (counted as 1.242 mmol/g, 15.7 g) was added, and toluene was distilled off under reduced pressure to weigh out the crude product of 1-(3-methoxyphenyl)-2,5-dimethylpyrrole (4-5) (counted as 19.5 mmol, 1.0 eq.). To this flask, a three-way stopcock, a Teflon®-coated magnetic stirring bar, a dropping funnel, and a thermometer were attached, and then the inside was purged with nitrogen. Anhydrous THF (40 mL) was added, and the obtained reactant solution was cooled to 5° C. by use of an ice-water bath. Subsequently, a n-BuLi/n-hexane solution (1.60 mol/L, 12.8 mL, 20.5 mmol, 1.05 eq.) was placed in the dropping funnel, and added dropwise over 10 minutes, while the reactant solution was being stirred, and the inside temperature was being kept at 10° C. or below. Then, the dropping funnel was rinsed with anhydrous n-hexane (1 mL). The obtained brown suspension was stirred at 5° C. for 1 hour. Then, an anhydrous THF (10 mL) solution of Cy$_2$PCl (5.0 g, 21.5 mmol, 1.1 eq.) was placed in the dropping funnel, and added dropwise over 15 minutes, while the suspension was being stirred, and the inside temperature was being kept at 10° C. or below. After completion of the dropwise addition, the reaction solution was stirred at 5° C. for 30 minutes.

(Post Treatment and Purification) The obtained suspension was concentrated under reduced pressure, and toluene and an aqueous solution of sodium hydrogen carbonate (1.6 g, approximately 1 eq.) were added to the residue (the mixture turned black upon the addition). The mixture was transferred to a separating funnel, shaken and allowed to stand, and the layers were separated. The organic layer was further washed twice with water. The solvent was distilled off from the organic layer under reduced pressure, and the precipitated crude crystals were washed by adding methanol and then filtered. The crude crystals were purified by recrystallization from toluene/methanol to give 5.0 g of title compound (1-7) as a colorless powder. Two Steps Overall Isolated Yield: 64.5%.

$^1$H NMR (300 MHz, CDCl$_3$): δ=7.38 (t, J=7.8 Hz, 1H), 6.90 (d, J=8.4 Hz, 1H), 6.77 (ddd, J=1.2, 3.9, 7.8 Hz, 1H), 5.89 (s, 2H), 3.88 (s, 3H), 2.32-2.16 (m, 2H), 1.98 (s, 6H), 1.86-1.56 (m, 8H), 1.47-0.89 (m, 12H).

$^{31}$P NMR (121 MHz, CDCl$_3$): δ=−4.7.

As can be seen from Examples 1 to 7, phosphorus compounds (1) of the present invention can be easily synthesized by deprotonation of N-arylazoles (4) with n-BuLi and then reaction with phosphorus compounds (5). In theory, 1-bromobutane is not by-produced in this reaction, and the side reaction (n-butylation), which caused the problem in the reference examples, does not occur. Hence, this reaction does not require the extremely low-temperature condition. In addition, N-arylazoles (4), which are raw materials of phosphorus compounds (1) of the present invention, can be synthesized easily and highly selectively at low costs by various approaches (Example 7: route 1 in Reaction Formula 2, Examples 1, 4, and 6: route 2 in Reaction Formula 2, and Example 5: route 3 in Reaction Formula 2), and also the crude products, as they are, can be used for production of phosphorus compounds (1) of the present invention without isolation or purification, although some exceptions exist. Accordingly, phosphorus compound (1) of the present invention is apparently better than conventional compound (2) in that phosphorus compound (1) of the present invention can be mass produced easily at low costs.

Example 8

Synthesis of (π-allyl) [N-(2-dicyclohexylphosphino-3-methoxyphenyl)carbazole]palladium(II) chloride (Structural Formula (3-1)) (Reaction Formula 12)

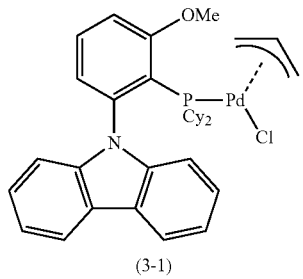

(3-1)

(Setting-Up and Reaction) To a 50 mL two-necked round-bottomed flask, [PdCl(π-allyl)]$_2$ (10.0 mg, 1.0 eq.) and N-(2-dicyclohexylphosphino-3-methoxyphenyl)carbazole (1-1) (25.7 mg, 2.0 eq.) were added. A three-way stopcock was attached to the flask, and the inside was purged with nitrogen. Subsequently, CDCl$_3$ (2 mL) was added, and the mixture was shaken at room temperature for 1 minute to obtain a CDCl$_3$ solution of title compound (3-1) as a pale yellow liquid. Reaction Conversion: 100% ($^{31}$P NMR).

$^1$H NMR (300 MHz, CDCl$_3$): δ=8.05 (d, J=7.8 Hz, 2H), 7.49 (t, J=7.8 Hz, 1H), 7.44-6.90 (br m, 7H), 6.64 (ddd, J=0.6, 3.0, 7.8 Hz, 1H), 4.85-4.60 (br m, 1H), 4.10 (t, 7.2 Hz, 1H), 3.98 (s, 3H), 3.30-2.80 (br m, 1H), 2.70-2.20 (br m, 3H), 2.10-0.80 (br m, 21H).

$^{31}$P NMR (121 MHz, CDCl$_3$): δ=27.6.

Note that CDCl$_3$ was used as the reaction solvent for simplifying the analysis in this example, but a general-purpose solvent such as THF can be used instead of expensive CDCl$_3$ when complex (3-1) of the present invention is actually used as a catalyst for an organic synthesis reaction. See Example 11.

Example 9

Synthesis of (π-allyl) [N-(2-diisopropylphosphino-3-methoxyphenyl)carbazole]palladium(II) chloride (Structural Formula (3-2)) (Reaction Formula 13)

Reaction Formula 12

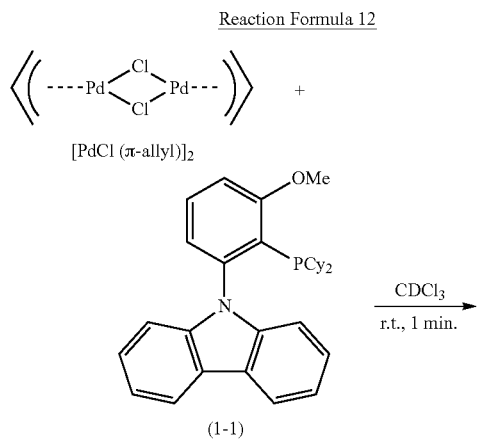

Reaction Formula 13

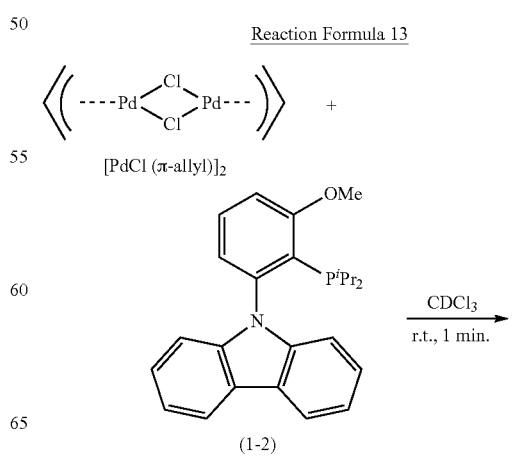

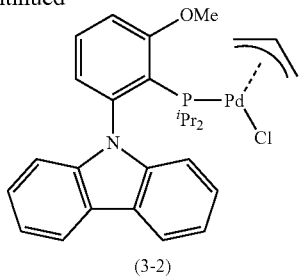

(3-2)

A CDCl$_3$ solution of title compound (3-2) was obtained as a pale yellow liquid by the same procedure as in Example 8, except that N-(2-diisopropylphosphino-3-methoxyphenyl)carbazole (1-2) was used instead of N-(2-dicyclohexylphosphino-3-methoxyphenyl)carbazole (1-1). Reaction Conversion: 100% ($^{31}$P NMR).

$^1$H NMR (300 MHz, CDCl$_3$): δ=8.05 (d, J=7.5 Hz, 2H), 7.51 (t, J=8.4 Hz, 1H), 7.47-6.84 (br m, 7H), 6.63 (ddd, J=0.9, 3.3, 7.8 Hz, 1H), 4.66-4.38 (br m, 1H), 4.04 (t, J=7.2 Hz, 1H), 4.01 (s, 3H), 3.40-2.80 (brm, 3H), 2.38 (br dd, J=9.9, 12.9 Hz, 1H), 1.48-0.90 (br m, 13H).
$^{31}$P NMR (121 MHz, CDCl$_3$): δ=36.4.

Example 10

Synthesis of (π-allyl) [N-(2-diphenylphosphino-3-methoxyphenyl)carbazole]palladium(II) chloride (Structural Formula (3-3)) (Reaction Formula 14)

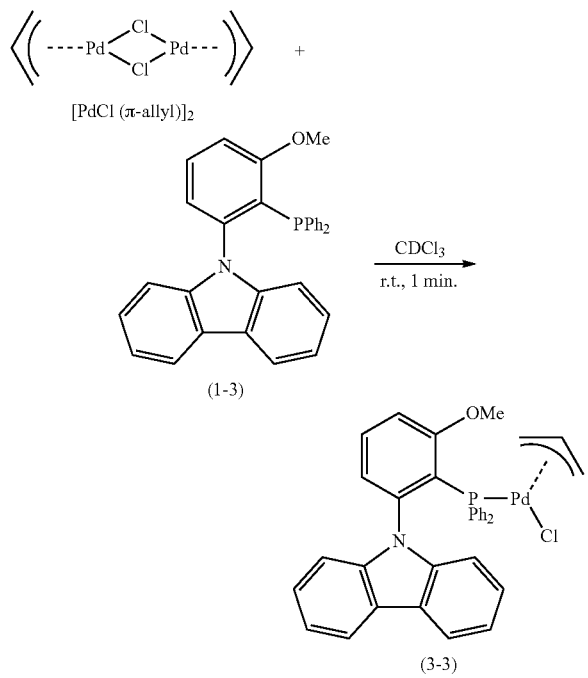

A CDCl$_3$ solution of title compound (3-3) was obtained as a pale yellow liquid by the same procedure as in Example 8, except that N-(2-diphenylphosphino-3-methoxyphenyl)carbazole (1-3) was used instead of N-(2-dicyclohexylphosphino-3-methoxyphenyl)carbazole (1-1). Reaction Conversion: 100% ($^{31}$P NMR).

$^1$H NMR (300 MHz, CDCl$_3$): δ=7.67 (br t, J=7.2 Hz, 2H), 7.61 (t, J=8.1 Hz, 1H), 7.28-7.13 (br m, 7H), 7.12-7.02 (br m, 4H), 7.00-6.90 (br m, 2H), 6.83-6.70 (br m, 5H), 5.56-5.38 (m, 1H), 4.63 (t, J=6.9 Hz, 1H), 3.78 (s, 3H), 3.55 (dd, J=10.2, 13.5 Hz, 1H), 3.27 (d, J=5.7 Hz, 1H), 2.74 (d, J=11.7 Hz, 1H)
$^{31}$P NMR (121 MHz, CDCl$_3$): δ=16.0.

Example 11

Synthesis of 4-Methylbiphenyl (Structural Formula (9)) by Suzuki-Miyaura Coupling Reaction of 4-Chlorobenzene with Phenylboronic Acid Using Phosphorus Compound (1-1) of the Present Invention as Ligand (Reaction Formula 15)

Reaction Formula 15

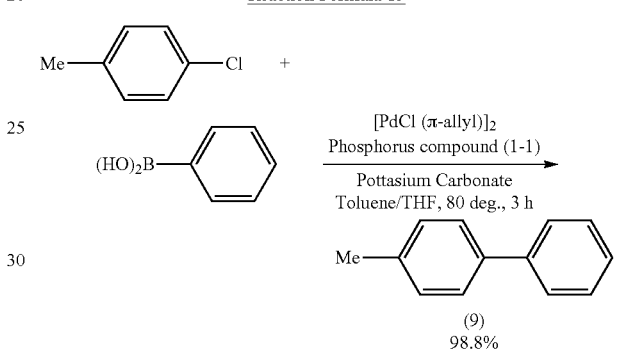

(9)
98.8%

(Setting-Up and Reaction) To a 50 mL two-necked round-bottomed flask, [PdCl(π-allyl)]$_2$ (5.9 mg, 0.025 mol %) and N-(2-dicyclohexylphosphino-3-methoxyphenyl)carbazole (1-1) (30.8 mg, 0.1 mol %) were added. A three-way stopcock was attached to the flask, and the inside was purged with nitrogen. Subsequently, anhydrous THF (6.5 mL) was added, and the mixture was shaken at room temperature for 1 minute to prepare a THF solution of a mixture of (π-allyl) [N-(2-dicyclohexylphosphino-3-methoxyphenyl)carbazole]palladium(II) chloride (3-1) (0.05 mol %) and N-(2-dicyclohexylphosphino-3-methoxyphenyl)carbazole (1-1) (0.05 mol %) as a pale yellow liquid (6.5 mL) (hereinafter, this solution is abbreviated as catalyst solution of Example 11). On the other hand, to a 200 mL four-necked round-bottomed flask, a three-way stopcock, a Teflon®-coated magnetic stirring bar, a condenser, and a thermometer were attached, and the inside was purged with nitrogen. To this flask, toluene (65 mL), 4-chlorotoluene (7.7 mL, 65.1 mmol, 1.0 eq.), phenylboronic acid (purity: 95%, 10.0 g, 78.0 mmol, 1.2 eq.), potassium carbonate (13.5 g, 97.5 mmol, 1.5 eq.), and the catalyst solution of Example 11 (6.5 mL) were sequentially added, and the mixture was stirred at 80° C. for 3 hours.

(Post Treatment and Purification) After the reaction mixture had been cooled to room temperature, water was added. The mixture was transferred to a separating funnel, shaken and allowed to stand, and the layers were separated. The organic layer was concentrated under reduced pressure. The obtained residue was purified by silica gel column chromatography (Eluent: n-hexane/toluene=4/1) to give 10.8 g of the desired title compound (9) as a colorless solid. Isolated Yield: 98.8%.

Example 12

Synthesis of 4-Methylbiphenyl (9) Using Phosphorus Compound (1-4) of the Present Invention as Ligand

Title compound (9) (10.9 g) was obtained by conducting a reaction for 3 hours using N-(2-dicyclohexylphosphino-3-isopropoxyphenyl)carbazole (1-4) as a ligand in exactly the same manner as in Example 11. Isolated Yield: 99.7%.

Example 13

Synthesis of 4-Methylbiphenyl (9) Using Phosphorus Compound (1-5) of the Present Invention as Ligand

Title compound (9) (9.2 g) was obtained by conducting a reaction for 3 hours using N-(2-dicyclohexylphosphino-3-tert-butoxyphenyl)carbazole (1-5) as a ligand in exactly the same manner as in Example 11. Isolated Yield: 84.1%.

Comparative Example 1

Synthesis of 4-Methylbiphenyl (9) Using Conventional Compound (2-1) as Ligand

Title compound (9) (4.8 g) was obtained by conducting a reaction for 3 hours using N-(2-dicyclohexylphosphinophenyl)carbazole (2-1) as a ligand in exactly the same manner as in Example 11. Isolated Yield: 43.9%.

Comparative Example 2

Synthesis of 4-Methylbiphenyl (9) Using Conventional Compound (2-2) as Ligand

Title compound (9) (3.5 g) was obtained by conducting a reaction for 3 hours using N-(2-di-tert-butylphosphinophenyl)carbazole (2-2) as a ligand in exactly the same manner as in Example 11. Isolated Yield: 32.0%.

Example 14

Synthesis of 4-Methylbiphenyl (9) Using Phosphorus Compound (1-7) of the Present Invention as Ligand

Title compound (9) (10.8 g) was obtained by conducting a reaction for 1 hour using 1-(2-dicyclohexylphosphino-3-methoxyphenyl)-2,5-dimethylpyrrole (1-7) as a ligand in exactly the same manner as in Example 11. Isolated Yield: 98.8%.

The results of Examples 11 to 14 and Comparative Examples 1 and 2 are summarized in Diagram 1 below.

| Ex./Comp. Ex. | Ligand | Reaction Time | Isolated Yield |
| --- | --- | --- | --- |
| Example 11 | (1-1) | 3 hours | 98.8% |
| Example 12 | (1-4) | 3 hours | 99.7% |
| Example 13 | (1-5) | 3 hours | 84.1% |
| Comp. Ex. 1 | (2-1) | 3 hours | 43.9% |
| Comp. Ex. 2 | (2-2) | 3 hours | 32.0% |
| Example 14 | (1-7) | 1 hour | 98.8% |

Diagram 1
Ligands:

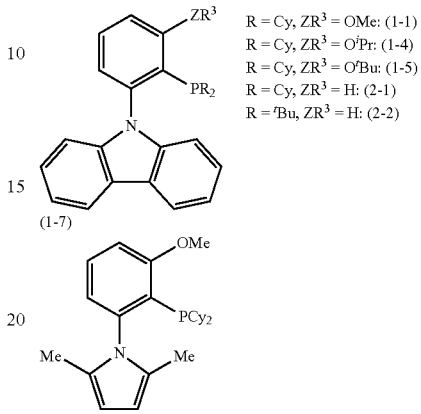

$R = Cy, ZR^3 = OMe: (1-1)$
$R = Cy, ZR^3 = O^iPr: (1-4)$
$R = Cy, ZR^3 = O^tBu: (1-5)$
$R = Cy, ZR^3 = H: (2-1)$
$R = {}^tBu, ZR^3 = H: (2-2)$

Here, Examples 11 to 14 and Comparative Examples 1 and 2 are reviewed. In each of the cases where conventional compound (2-1) or (2-2) was used as the ligand, the isolated yield of 4-methylbiphenyl was only 32.0 to 43.9%. On the other hand, in each of the cases where phosphorus compound (1-1), (1-4), or (1-5) of the present invention having the same structure as that of these conventional compounds except for the $R^3Z$ group was used as the ligand, the isolated yield of the 4-methylbiphenyl was 84.1 to 99.7%, and it was found that the activity was improved by at least 1.92 times or more. Moreover, it was also found that the use of phosphorus compound (1-7), in which the 2,5-dimethyl-1H-pyrrol-1-yl group was introduced instead of the 9H-carbazol-9-yl group, further improved the reaction rate, and 4-methylbiphenyl was obtained quantitatively within 1 hour. Accordingly, phosphorus compound (1) of the present invention is better than conventional compound (2) not only in terms of the ease of production but also from the viewpoint of activity as a ligand.

Example 15

Synthesis of N-(4-Methoxyphenyl)Morpholine (Structural Formula (10)) by Buchwald-Hartwig Reaction of 4-Chloroanisole with Morpholine Using Phosphorus Compound (1-4) of the Present Invention as a Ligand (Reaction Formula 16)

Reaction Formula 16

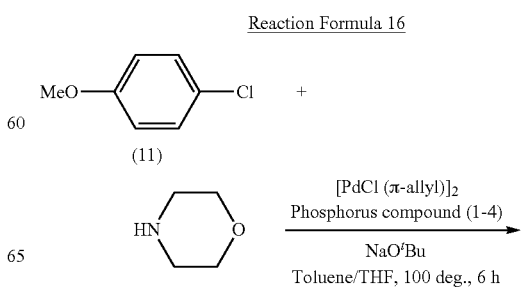

-continued

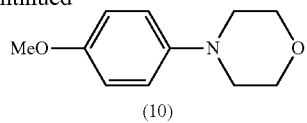

Impurities:

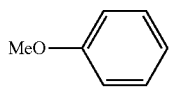

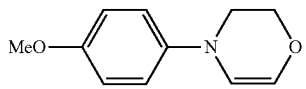

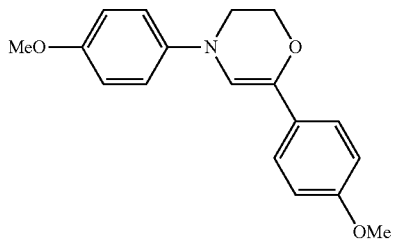

(Setting-Up and Reaction) To a 50 mL two-necked round-bottomed flask, [PdCl(π-allyl)]$_2$ (4.6 mg, 0.025 mol %) and N-(2-dicyclohexylphosphino-3-isopropoxyphenyl)carbazole (1-4) (24.9 mg, 0.1 mol %) were added. A three-way stopcock was attached to the flask, and the inside was purged with nitrogen. Subsequently, anhydrous THF (5.0 mL) was added, and the mixture was shaken at room temperature for 1 minute to prepare a THF solution of a mixture of (π-allyl)[N-(2-dicyclohexylphosphino-3-isopropoxyphenyl)carbazole]palladium(II) chloride (3-4) (0.05 mol %) and N-(2-dicyclohexylphosphino-3-isopropoxyphenyl)carbazole (1-4) (0.05 mol %) as a pale yellow liquid (5.0 mL) (hereinafter, this liquid is abbreviated as catalyst solution of Example 15). On the other hand, to a 100 mL four-necked round-bottomed flask, a three-way stopcock, a Teflon®-coated magnetic stirring bar, a condenser, and a thermometer were attached, and the inside was purged with nitrogen. To this flask, toluene (50 mL), NaO$^t$Bu (5.8 g, 60.0 mmol, 1.2 eq.), 4-chloroanisole (11) (6.1 mL, 50.0 mmol, 1.0 eq.), morpholine (4.6 mL, 52.5 mmol, 1.05 eq.), and the catalyst solution of Example 15 (5.0 mL) were sequentially added, and the mixture was stirred at 100° C. for 6 hours.

(Analysis) A sample (approximately 50 μL) of the reaction solution was taken out, and diluted with toluene (approximately 1 mL). Then, the diluted sample was washed with a saturated aqueous ammonium chloride solution (approximately 0.5 mL) and water (approximately 0.5 mL), and then analyzed by GC. GC retention times were as follows:
4-chloroanisole (11): 3.80 minutes
N-(4-methoxyphenyl)morpholine (10): 10.27 minutes
Impurity (12): 2.59 minutes
Impurity (13): 10.42 minutes
Impurity (14): 26.66 minutes.

Comparative Example 3

Synthesis of N-(4-Methoxyphenyl)Morpholine (Structural Formula (10)) Using Conventional Compound (2-1) as Ligand Exactly the same experiment as in Example 15 was conducted except that N-(2-dicyclohexylphosphinophenyl)carbazole (2-1) was used as a ligand instead of N-(2-dicyclohexylphosphino-3-isopropoxyphenyl)carbazole (1-4), and the reaction solution was analyzed by GC.

Table 1 below shows the GC analysis results of Example 15 and Comparative Example 3.

TABLE 1

| Ex./ | | GC area (%) | | | | | | |
|---|---|---|---|---|---|---|---|---|
| Comp. Ex. | Ligand | (11) | (10) | (12) | (13) | (14) | Impurities (total) | Others |
| Ex. 15 | (1-4) | 0.04 | 98.74 | 0.26 | 0.19 | 0 | 0.45 | 0.77 |
| Comp. Ex. 3 | (2-1) | 0.61 | 93.66 | 1.79 | 1.10 | 1.98 | 4.87 | 0.86 |

In the case where conventional compound (2-1) was used as the ligand, 4.87%, in total, of Impurities (12), (13), and (14) were by-produced due to the β-elimination of morpholine, and hence the selectivity for the target product, N-(4-methoxyphenyl)morpholine (10), was only 93.66% (Comparative Example 3). On the other hand, in the case where phosphorus compound (1-4) of the present invention was used as the ligand, the total amount of impurities (12), (13), and (14) by-produced was 0.45%, and the selectivity for target product (10) was improved to 98.74% (Example 15). Accordingly, phosphorus compound (1) of the present invention was better than conventional compound (2) not only in terms of the ease of production and the high activity but also from the viewpoint of the reaction selectivity in the use as a ligand.

Phosphorus compound (1) of the present invention is useful as a ligand for catalytic organic synthesis reactions using transition metal species, and moreover can be produced easily. Complex (3) of the present invention is useful as a catalyst for organic synthesis reactions. For example, a complex of palladium, which is one of the transition metals, and phosphorus compound (1) of the present invention is extremely useful as a catalyst for cross-coupling reactions and the like, and these reactions make it possible to efficiently produce aromatic compounds and the like.

The invention claimed is:
1. A phosphorus compound represented by general formula (1):

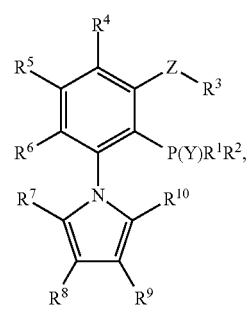

wherein
R$^1$ and R$^2$ each independently represent a hydrogen atom, an alkyl group, an alkenyl group, an aryl group, a heteroaryl group, an aralkyl group, an alkoxy group, or a halogeno group, in which the alkenyl group, the aryl group, the heteroaryl group, the aralkyl group, and the alkoxy group are optionally substituted with at least one group selected from the group consisting of an alkyl group, a halogenoalkyl group, an aryl group, a heteroaryl group, an aralkyl group, an alkoxy group, and a halogeno group;

$R^3$ represents an alkyl group, an aryl group, or an aralkyl group, in which the aryl group and the aralkyl group are optionally substituted with at least one group selected from the group consisting of an alkyl group, an aryl group, and an aralkyl group;

$R^4$, $R^5$, $R^6$, $R^7$, $R^8$, $R^9$, and $R^{10}$ each independently represent a hydrogen atom, an alkyl group, an alkenyl group, an aryl group, or an aralkyl group, in which the alkenyl group, the aryl group, and the aralkyl group are optionally substituted with at least one group selected from the group consisting of an alkyl group, an aryl group, and an aralkyl group;

N represents a nitrogen atom;

P represents a phosphorus atom;

Y represents lone pair electrons, an oxo group, or a thioxo group;

Z represents an oxy group or a thioxy group;

$R^1$ and $R^2$ may be bonded to each other to form a P-containing ring, in which the ring is optionally substituted with at least one group selected from the group consisting of an alkyl group, a halogenoalkyl group, an aryl group, a heteroaryl group, an aralkyl group, an alkoxy group, and a halogeno group; and each of the pairs of $R^4$ and $R^5$, $R^5$ and $R^6$, $R^7$ and $R^8$, $R^8$ and $R^9$, and $R^9$ and $R^{10}$ may be bonded to each other to form an unsaturated hydrocarbon ring which is fused with the benzene ring or the pyrrole ring, in which the unsaturated hydrocarbon ring is optionally substituted with at least one group selected from the group consisting of an alkyl group, an aryl group, and an aralkyl group.

2. The phosphorus compound according to claim 1, wherein $R^1$ and $R^2$ each independently represent an alkyl group, an alkenyl group, an aryl group, a heteroaryl group which may have a substituent(s), or an aralkyl group, in which the alkenyl group, the aryl group, the heteroaryl group, and the aralkyl group are optionally substituted with at least one group selected from the group consisting of an alkyl group, a halogenoalkyl group, an aryl group, a heteroaryl group, an aralkyl group, an alkoxy group, and a halogeno group; and Y is lone pair electrons.

3. The phosphorus compound according to claim 1, wherein

Z is an oxy group.

4. A transition metal complex comprising:
a transition metal; and
the phosphorus compound according to claim 1 as a ligand.

5. The transition metal complex according to claim 4, wherein
the transition metal is selected from the group consisting of iron, cobalt, nickel, copper, ruthenium, rhodium, palladium, silver, osmium, iridium, platinum, and gold.

6. The transition metal complex according to claim 5, wherein
the transition metal is palladium.

* * * * *